(12) United States Patent
Gharib et al.

(10) Patent No.: US 8,740,783 B2
(45) Date of Patent: Jun. 3, 2014

(54) SYSTEM AND METHODS FOR PERFORMING NEUROPHYSIOLOGIC ASSESSMENTS WITH PRESSURE MONITORING

(75) Inventors: James Gharib, San Diego, CA (US); Allen Farquhar, Portland, OR (US); Scot Martinelli, Mountain Top, PA (US); David Ivanko, San Diego, CA (US); Benjamin VerHage, Paramus, NJ (US)

(73) Assignee: NuVasive, Inc., San Diego, CA (US)

( * ) Notice: Subject to any disclaimer, the term of this patent is extended or adjusted under 35 U.S.C. 154(b) by 1277 days.

(21) Appl. No.: 11/490,717

(22) Filed: Jul. 20, 2006

(65) Prior Publication Data

US 2007/0021682 A1    Jan. 25, 2007

Related U.S. Application Data

(60) Provisional application No. 60/701,305, filed on Jul. 20, 2005.

(51) Int. Cl.
*A61B 1/32* (2006.01)

(52) U.S. Cl.
USPC .............................. 600/202; 607/48; 600/554

(58) Field of Classification Search
USPC ......... 600/300, 372, 373, 381, 382, 393, 546, 600/547, 550, 554, 557, 561, 587, 594, 595, 600/184, 201, 202, 210, 213, 226; 606/1, 606/32, 41, 86 R, 86 A; 607/1, 2, 43, 48; 73/172; 702/1, 19, 127, 138, 139
See application file for complete search history.

(56) References Cited

U.S. PATENT DOCUMENTS

| | | | |
|---|---|---|---|
| 972,983 | A | 10/1910 | Arthur |
| 1,328,624 | A | 1/1920 | Graham |
| 1,548,184 | A | 8/1925 | Cameron |
| 2,704,064 | A | 6/1955 | Fizzell et al. |
| 2,736,002 | A | 2/1956 | Oriel |
| 2,808,826 | A | 10/1957 | Reiner et al. |
| 3,364,929 | A | 1/1968 | Ide et al. |
| 3,664,329 | A | 5/1972 | Naylor |
| 3,682,162 | A | 8/1972 | Colyer |

(Continued)

FOREIGN PATENT DOCUMENTS

| | | |
|---|---|---|
| DE | 299 08 259 | 7/1999 |
| EP | 0 759 307 | 2/1997 |

(Continued)

OTHER PUBLICATIONS

"Electromyography System," International Search report from International Application No. PCT/US00/32329, Apr. 27, 2001, 9 pages.

(Continued)

*Primary Examiner* — Max Hindenburg
*Assistant Examiner* — Renee Danega
(74) *Attorney, Agent, or Firm* — Jonathan Spangler; Heather Prado

(57) ABSTRACT

Systems and methods for performing neurophysiologic assessments of neural tissue including nerve pathology monitoring which may or may not be augmented by adding the ability to assess or monitor the pressure being exerted upon a nerve or nerve root before, during and/or after retraction.

20 Claims, 18 Drawing Sheets

(56) References Cited

U.S. PATENT DOCUMENTS

| | | |
|---|---|---|
| 3,785,368 A | 1/1974 | McCarthy et al. |
| 3,830,226 A | 8/1974 | Staub et al. |
| 3,957,036 A | 5/1976 | Normann |
| 4,099,519 A | 7/1978 | Warren |
| 4,164,214 A | 8/1979 | Stark et al. |
| 4,207,897 A | 6/1980 | Lloyd et al. |
| 4,224,949 A | 9/1980 | Scott et al. |
| 4,226,228 A | 10/1980 | Shin et al. |
| 4,235,242 A | 11/1980 | Howson et al. |
| 4,285,347 A | 8/1981 | Hess |
| 4,291,705 A | 9/1981 | Severinghaus et al. |
| 4,461,300 A | 7/1984 | Christensen |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,018 A | 6/1986 | Rantala |
| 4,616,660 A | 10/1986 | Johns |
| 4,633,889 A | 1/1987 | Talalla |
| 4,658,835 A | 4/1987 | Pohndorf |
| 4,744,371 A | 5/1988 | Harris |
| 4,759,377 A | 7/1988 | Dykstra |
| 4,784,150 A | 11/1988 | Voorhies et al. |
| 4,807,642 A | 2/1989 | Brown |
| 4,892,105 A | 1/1990 | Prass |
| 4,926,865 A | 5/1990 | Oman |
| 4,962,766 A | 10/1990 | Herzon |
| 4,964,411 A | 10/1990 | Johnson et al. |
| 5,007,902 A | 4/1991 | Witt |
| 5,058,602 A | 10/1991 | Brody |
| 5,081,990 A | 1/1992 | Deletis |
| 5,092,344 A | 3/1992 | Lee |
| 5,125,406 A | 6/1992 | Goldstone et al. |
| 5,127,403 A | 7/1992 | Brownlee |
| 5,161,533 A | 11/1992 | Prass et al. |
| 5,196,015 A | 3/1993 | Neubardt |
| 5,201,325 A * | 4/1993 | McEwen et al. ............. 600/587 |
| RE34,390 E | 9/1993 | Culver |
| 5,255,691 A | 10/1993 | Otten |
| 5,282,468 A | 2/1994 | Klepinski |
| 5,284,153 A | 2/1994 | Raymond et al. |
| 5,284,154 A | 2/1994 | Raymond et al. |
| 5,299,563 A | 4/1994 | Seton |
| 5,312,417 A | 5/1994 | Wilk |
| 5,313,956 A | 5/1994 | Knutsson et al. |
| 5,313,962 A | 5/1994 | Obenchain |
| 5,327,902 A | 7/1994 | Lemmen |
| 5,333,618 A | 8/1994 | Lekhtman et al. |
| 5,375,067 A | 12/1994 | Berchin |
| 5,383,876 A | 1/1995 | Nardella |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,540,235 A | 7/1996 | Wilson |
| 5,549,656 A | 8/1996 | Reiss |
| 5,560,372 A | 10/1996 | Cory |
| 5,566,678 A | 10/1996 | Cadwell |
| 5,569,248 A | 10/1996 | Mathews |
| 5,579,781 A | 12/1996 | Cooke |
| 5,593,429 A | 1/1997 | Ruff |
| 5,599,279 A | 2/1997 | Slotman et al. |
| 5,601,608 A | 2/1997 | Mouchawar |
| 5,630,813 A | 5/1997 | Kieturakis |
| 5,671,752 A | 9/1997 | Sinderby et al. |
| 5,707,359 A | 1/1998 | Bufalini |
| 5,711,307 A | 1/1998 | Smits |
| 5,728,046 A | 3/1998 | Mayer et al. |
| 5,741,253 A | 4/1998 | Michelson |
| 5,759,159 A | 6/1998 | Masreliez |
| 5,769,781 A | 6/1998 | Chappuis |
| 5,772,661 A | 6/1998 | Michelson |
| 5,775,331 A | 7/1998 | Raymond et al. |
| 5,776,144 A | 7/1998 | Leysieffer et al. |
| 5,779,642 A | 7/1998 | Nightengale |
| 5,785,658 A | 7/1998 | Benaron |
| 5,797,854 A | 8/1998 | Hedgecock |
| 5,814,073 A | 9/1998 | Bonutti |
| 5,830,151 A | 11/1998 | Hadzic et al. |
| 5,851,191 A | 12/1998 | Gozani |
| 5,853,373 A | 12/1998 | Griffith et al. |
| 5,860,973 A | 1/1999 | Michelson |
| 5,862,314 A | 1/1999 | Jeddeloh |
| 5,872,314 A | 2/1999 | Clinton |
| 5,885,219 A | 3/1999 | Nightengale |
| 5,888,196 A | 3/1999 | Bonutti |
| 5,902,231 A | 5/1999 | Foley et al. |
| 5,928,139 A | 7/1999 | Koros et al. |
| 5,928,158 A | 7/1999 | Aristides |
| 5,976,094 A | 11/1999 | Gozani et al. |
| 6,004,262 A | 12/1999 | Putz et al. |
| 6,011,985 A | 1/2000 | Athan et al. |
| 6,027,456 A | 2/2000 | Feler et al. |
| 6,038,469 A | 3/2000 | Karlsson et al. |
| 6,038,477 A | 3/2000 | Kayyali |
| 6,050,992 A | 4/2000 | Nichols |
| 6,074,343 A | 6/2000 | Nathanson et al. |
| 6,104,957 A | 8/2000 | Alo et al. |
| 6,104,960 A | 8/2000 | Duysens et al. |
| 6,119,068 A | 9/2000 | Kannonji |
| 6,120,503 A | 9/2000 | Michelson |
| 6,126,660 A | 10/2000 | Dietz |
| 6,128,576 A | 10/2000 | Nishimoto |
| 6,132,386 A | 10/2000 | Gozani et al. |
| 6,132,387 A | 10/2000 | Gozani et al. |
| 6,135,965 A | 10/2000 | Tumer et al. |
| 6,139,493 A | 10/2000 | Koros et al. |
| 6,139,545 A | 10/2000 | Utley |
| 6,146,335 A | 11/2000 | Gozani |
| 6,161,047 A | 12/2000 | King et al. |
| 6,181,961 B1 | 1/2001 | Prass |
| 6,206,826 B1 | 3/2001 | Mathews et al. |
| 6,210,324 B1 | 4/2001 | Reno |
| 6,224,549 B1 | 5/2001 | Drongelen |
| 6,259,945 B1 * | 7/2001 | Epstein et al. ............. 600/547 |
| 6,266,558 B1 | 7/2001 | Gozani et al. |
| 6,273,905 B1 | 8/2001 | Streeter |
| 6,292,701 B1 | 9/2001 | Prass et al. |
| 6,306,100 B1 | 10/2001 | Prass |
| 6,312,392 B1 | 11/2001 | Herzon |
| 6,325,764 B1 | 12/2001 | Griffith et al. |
| 6,334,068 B1 | 12/2001 | Hacker |
| 6,346,078 B1 | 2/2002 | Ellman |
| 6,348,058 B1 | 2/2002 | Melkent et al. |
| 6,393,325 B1 | 5/2002 | Mann et al. |
| 6,425,859 B1 | 7/2002 | Foley et al. |
| 6,425,901 B1 | 7/2002 | Zhu et al. |
| 6,451,015 B1 | 9/2002 | Rittman, III et al. |
| 6,466,817 B1 | 10/2002 | Kaula et al. |
| 6,500,128 B2 | 12/2002 | Marino |
| 6,507,755 B1 | 1/2003 | Turner et al. |
| 6,546,271 B1 * | 4/2003 | Reisfeld ............. 600/407 |
| 6,564,078 B1 | 5/2003 | Marino et al. |
| 6,579,244 B2 | 6/2003 | Goodwin |
| 6,582,441 B1 | 6/2003 | He et al. |
| 6,585,638 B1 | 7/2003 | Yamamoto |
| 6,618,626 B2 | 9/2003 | West et al. |
| 6,719,692 B2 | 4/2004 | Kleffner et al. |
| 6,730,021 B2 | 5/2004 | Vassiliades et al. |
| 6,760,616 B2 | 7/2004 | Hoey et al. |
| 6,770,074 B2 | 8/2004 | Michelson |
| 6,796,985 B2 | 9/2004 | Bolger et al. |
| 6,819,956 B2 | 11/2004 | DiLorenzo |
| 6,847,849 B2 | 1/2005 | Mamo et al. |
| 6,849,047 B2 | 2/2005 | Goodwin |
| 6,855,105 B2 | 2/2005 | Jackson, III et al. |
| 6,902,569 B2 | 6/2005 | Parmer et al. |
| 6,916,294 B2 | 7/2005 | Ayad |
| 6,926,728 B2 | 8/2005 | Zucherman et al. |
| 6,929,606 B2 | 8/2005 | Ritland |
| 7,050,848 B2 | 5/2006 | Hoey et al. |

(56) References Cited

U.S. PATENT DOCUMENTS

| | | | |
|---|---|---|---|
| 7,079,883 B2 | 7/2006 | Marino et al. | |
| 7,089,059 B1 | 8/2006 | Pless | |
| 7,153,279 B2 | 12/2006 | Ayad | |
| 7,177,677 B2 | 2/2007 | Kaula et al. | |
| 7,207,949 B2 | 4/2007 | Miles et al. | |
| 7,258,688 B1 | 8/2007 | Shah et al. | |
| 7,294,127 B2 | 11/2007 | Leung et al. | |
| 7,306,563 B2 * | 12/2007 | Huang | 600/500 |
| 7,310,546 B2 | 12/2007 | Prass | |
| D621,041 S | 8/2010 | Mao et al. | |
| 7,775,974 B2 | 8/2010 | Buckner | |
| 2001/0039949 A1 | 11/2001 | Loubser | |
| 2001/0056280 A1 | 12/2001 | Underwood et al. | |
| 2002/0007129 A1 | 1/2002 | Marino | |
| 2002/0072686 A1 | 6/2002 | Hoey et al. | |
| 2002/0161415 A1 | 10/2002 | Cohen et al. | |
| 2002/0193843 A1 | 12/2002 | Hill et al. | |
| 2003/0032966 A1 | 2/2003 | Foley et al. | |
| 2003/0078618 A1 | 4/2003 | Fey et al. | |
| 2003/0105503 A1 | 6/2003 | Marino | |
| 2004/0199084 A1 | 10/2004 | Kelleher et al. | |
| 2004/0225228 A1 * | 11/2004 | Ferree | 600/554 |
| 2005/0004593 A1 | 1/2005 | Simonson | |
| 2005/0004623 A1 | 1/2005 | Miles et al. | |
| 2005/0075578 A1 | 4/2005 | Gharib et al. | |
| 2005/0080418 A1 | 4/2005 | Simonson et al. | |
| 2005/0119660 A1 | 6/2005 | Bourlion | |
| 2005/0182454 A1 | 8/2005 | Gharib et al. | |
| 2005/0256582 A1 | 11/2005 | Feree | |
| 2006/0025703 A1 | 2/2006 | Miles et al. | |
| 2006/0052828 A1 | 3/2006 | Kim et al. | |
| 2006/0069315 A1 | 3/2006 | Miles et al. | |
| 2006/0224078 A1 | 10/2006 | Hoey et al. | |
| 2007/0016097 A1 | 1/2007 | Farquhar et al. | |
| 2007/0198062 A1 | 8/2007 | Miles et al. | |
| 2007/0293762 A1 | 12/2007 | Marino | |
| 2008/0015612 A1 | 1/2008 | Urmey | |
| 2008/0039914 A1 | 2/2008 | Cory et al. | |
| 2008/0058606 A1 | 3/2008 | Miles et al. | |
| 2008/0064976 A1 | 3/2008 | Kelleher et al. | |
| 2008/0064977 A1 | 3/2008 | Kelleher et al. | |
| 2008/0065178 A1 | 3/2008 | Kelleher et al. | |
| 2008/0071191 A1 | 3/2008 | Kelleher et al. | |

FOREIGN PATENT DOCUMENTS

| | | |
|---|---|---|
| EP | 0 972 538 | 1/2000 |
| FR | 2 795 624 | 1/2001 |
| FR | 2 796 846 | 2/2001 |
| WO | 00/38574 | 7/2000 |
| WO | 00/66217 | 11/2000 |
| WO | 00/67645 | 11/2000 |
| WO | 01/03604 | 1/2001 |
| WO | 01/37728 | 5/2001 |
| WO | WO 03/005887 | 1/2003 |
| WO | WO 03/026482 | 3/2003 |
| WO | 03/037170 | 5/2003 |
| WO | WO 03/037170 | 8/2003 |
| WO | 2004/012809 | 2/2004 |
| WO | 2005/013805 | 2/2005 |
| WO | WO 2005/013805 | 2/2005 |
| WO | WO 2006/084193 | 2/2006 |
| WO | WO 2006/042075 | 4/2006 |
| WO | 2006/084193 | 8/2006 |

OTHER PUBLICATIONS

"Nerve Proximity and Status Detection System and Method," International Search Report from International Application No. PCT/US01/18606, Oct. 18, 2001, 6 pages.

"Relative Nerve Movement and Status Detection System and Method," International Search Report from International Application No. PCT/US01/18579, Jan. 15, 2002, 6 pages.

"System and Method for Determining Nerve Proximity Direction and Pathology During Surgery," International Search Report from International Application No. PCT/US02/22247, Mar. 27, 2003, 4 pages.

"System and Methods for Determining Nerve Direction to a Surgical Instrument," International Search Report from International Application No. PCT/US03/02056, Aug. 12, 2003, 5 pages.

"Systems and Methods for Performing Percutaneous Pedicle Integrity Assessments," International Search Report from International Application No. PCT/US02/35047, Aug. 11, 2003, 5 pages.

"Systems and Methods for Performing Surgery Procedures and Assessments," International Search Report from International Application No. PCT/US02/30617, Jun. 5, 2003, 4 pages.

"Systems and Methods for Performing Neurophysiologic Assessments During Spine Surgery," International Search Report from International Application No. PCT/US06/03966, Oct. 23, 2006, 5 pages.

"Multi-Channel Stimulation Threshold Detection Algorithm for Use in Neurophysiology Monitoring," International Search Report from International Application No. PCT/US06/37013, Mar. 19, 2007, 10 pages.

Lenke et al., "Triggered Electromyographic Threshold for Accuracy of Pedicle Screw Placement," *Spine*, 1995, 20(4): 1585-1591.

"Brackmann II EMG System," *Medical Electronics*, 1999, 4 pages.

"Neurovision SE Nerve Locator/Monitor", RLN Systems Inc. Operators Manual, 1999, 22 pages.

"The Brackmann II EMG Monitoring System," Medical Electronics Co. Operator's Manual Version 1.1, 1995, 50 pages.

"The Nicolet Viking IV," Nicolet Biomedical Products, 1999, 6 pages.

Anderson et al., "Pedicle screws with stimulus-evoked EMG," *Spine*, Department of Orthopaedic Surgery University of Virginia, Jul. 15, 2002, 27(14): 1577-1581.

Bose et al., "Neurophysiologic Monitoring of Spinal Nerve Root Function During Instrumented Posterior Lumber Spine Surgery," *Spine*, 2002, 27(13):1444-1450.

Calancie et al., "Stimulus-Evoked EMG Monitoring During Transpedicular Lumbosacral Spine Instrumentation" *Spine*, 1994, 19(24): 2780-2786.

Clements et al., "Evoked and Spontaneous Electromyography to Evaluate Lumbosacral Pedicle Screw Placement," *Spine*, 1996, 21(5): 600-604.

Danesh-Clough et al. ,"The Use of Evoked EMG in Detecting Misplaced Thoracolumbar Pedicle Screws," *Spine*, Orthopaedic Department Dunedin Hospital, Jun. 15, 2001, 26(12): 1313-1316.

Darden et al., "A Comparison of Impedance and Electromyogram Measurements in Detecting the Presence of Pedicle Wall Breakthrough," *Spine*, Charlotte Spine Center North Carolina, Jan. 15, 1998, 23(2): 256-262.

Ebraheim et al., "Anatomic Relations Between the Lumbar Pedicle and the Adjacent Neural Structures," *Spine*, Department of Orthopaedic Surgery Medical College of Ohio, Oct. 15, 1997, 22(20): 2338-2341.

Ford et al. "Electrical Characteristics of Peripheral Nerve Stimulators Implications for Nerve Localization," *Regional Anesthesia*, 1984, 9: 73-77.

Glassman et al., "A Prospective Analysis of Intraoperative Electromyographic Monitoring of Pedicle Screw Placement With Computed Tomographic Scan Confirmation," *Spine*, 1995, 20(12): 1375-1379.

Greenblatt et al., "Needle Nerve Stimulator-Locator: Nerve Blocks with a New Instrument for Locating Nerves," *Anesthesia& Analgesia*, 1962, 41(5): 599-602.

Haig, "Point of view," *Spine*, 2002, 27(24): 2819.

Haig et al., "The Relation Among Spinal Geometry on MRI, Paraspinal Electromyographic Abnormalities, and Age in Persons Referred for Electrodiagnostic Testing of Low Back Symptoms," *Spine*, Department of Physical Medicine and Rehabilitation University of Michigan, Sep. 1, 2002, 27(17): 1918-1925.

(56) References Cited

OTHER PUBLICATIONS

Holland et al., "Higher Electrical Stimulus Intensities are Required to Activate Chronically Compressed Nerve Roots: Implications for Intraoperative Electromyographic Pedicle Screw Testing," *Spine*, Department of Neurology, Johns Hopkins University School of Medicine, Jan. 15, 1998, 23(2): 224-227.

Holland, "Intraoperative Electromyography During Thoracolumbar Spinal Surgery," *Spine*, 1998, 23(17): 1915-1922.

Journee et al., "System for Intra-Operative Monitoring of the Cortical Integrity of the Pedicle During Pedicle Screw Placement in Low-Back Surgery: Design and Clinical Results," *Sensory and Neuromuscular Diagnostic Instrumentation and Data Analysis I, 18th Annual International Conference on Engineering in Medicine and Biology Society*, Amsterdam, 1996, pp. 144-145.

Maguire et al., "Evaluation of Intrapedicular Screw Position Using Intraoperative Evoked Electromyography," *Spine*, 1995, 20(9): 1068-1074.

Martin et al. "Initiation of Erection and Semen Release by Rectal Probe Electrostimulation (RPE)," *The Journal of Urology*, The Williams & Wilkins Co., 1983, 129: 637-642.

Minahan et al., "The Effect of Neuromuscular Spine, Department of Neurology, Johns Blockade on Pedicle Screw Stimulation Thresholds" Hopkins University School of Medicine, Oct. 1, 2000, 25(19): 2526-2530.

Pither et al., "The Use of Peripheral Nerve Stimulators for Regional Anesthesia: Review of Experimental Characteristics Technique and Clinical Applications," *Regional Anesthesia*, 1985, 10:49-58.

Raj et al., "Infraclavicular Brachial Plexus Block—A New Approach" *Anesthesia and Analgesia*, 1973, (52)6: 897-904.

Raj et al., "The Use of Peripheral Nerve Stimulators for Regional Anesthesia," *Clinical Issues in Regional Anesthesia*, 1985, 1(4):1-6.

Raj et al., "Use of the Nerve Stimulator for Peripheral Blocks," *Regional Anesthesia*, Apr.-Jun. 1980, pp. 14-21.

Raymond et al., "The Nerve Seeker: A System for Automated Nerve Localization," *Regional Anesthesia*, 1992, 17(3): 151-162.

Shafik, "Cavernous Nerve Simulation through an Extrapelvic Subpubic Approach: Role in Penile Erection," *Eur. Urol*, 1994, 26: 98-102.

Toleikis et al., "The Usefulness of Electrical Stimulation for Assessing Pedicle Screw Replacements," *Journal of Spinal Disorder*, 2000, 13(4): 283-289.

Moed et al., "Insertion of an iliosacral implant in an animal model," Journal of Bone and Joint Surgery, Nov. 1999, 81A(11): 1529-1537.

"NIM-Response, so advanced . . . yet so simple," XoMed, Inc., 1999, 12 pages.

Moed et al., "Intraoperative monitoring with stimulus-evoked electromyography during placement of iliosacral screws," The Journal of Bone and Joint Surgery, Apr. 1998, 81A(4): 10 pages.

"New data analyzer combines the functions of six instruments in one unit" News Release, Nov. 11, 1987, 3 pages.

"NuVasive's spine surgery system cleared in the US," Pharm & Medical Industry Week, Dec. 10, 2001, 1 page.

"Risk Capital Funds," *Innovation*, Mar. 6, 1990, 172: 3 pages.

* cited by examiner

SYSTEM AND METHODS FOR PERFORMING NEUROPHYSIOLOGIC ASSESSMENTS WITH PRESSURE MONITORING

CROSS REFERENCE TO RELATED APPLICATIONS

This application is a nonprovisional patent application claiming the benefit of priority from commonly owned U.S. Provisional Patent Application Ser. No. 60/701,305, entitled "System and Methods for Determining Nerve Proximity, Nerve Direction, and Nerve Pathology During Surgery," and filed on Jul. 20, 2005, the entire contents of which are expressly incorporated by reference into this disclosure as if set forth herein in its entirety.

BACKGROUND OF THE INVENTION

I. Field of the Invention

The present invention relates to a system and methods generally aimed at surgery. More particularly, the present invention is directed at a system and related methods for performing neurophysiologic assessments with additional pressure monitoring.

II. Description of Related Art

It has been estimated that somewhere between 50 and 70 million people suffer from chronic back pain in the United States. In most cases, conservative therapies, including, for example, bed rest and physical therapy will succeed in alleviating or at least significantly reducing the back pain. Still, a significant number of patients are unaided by conservative therapies alone and undergo spinal surgery before finding relief. The rate at which caregivers and patients opt for surgery also continues to grow as medical technology advances and surgical options increase. In all, approximately 750,000 spine surgeries are performed per year in the United States alone.

When necessary, spine surgery may provide great benefit to the patient, often allowing patients to resume activities long since abandoned because of the debilitating pain. Spine surgery, however, is not without risk. Operating on or near the spine generally means operating in close proximity to delicate neural tissue, such as the spinal cord and nerve roots. Often, in order to reach the surgical target site the delicate nerve tissue must be retracted out of the surgical corridor. A typical nerve retractor serves to pull or otherwise maintain the nerve outside the area of surgery, thereby protecting the nerve from inadvertent damage or contact by the "active" instrumentation used to perform the actual surgery. While generally advantageous in protecting the nerve, it has been observed that such retraction can cause nerve function to become impaired or otherwise pathologic over time due to the retraction. In certain surgical applications, such as spinal surgery, it is not possible to determine if such retraction is hurting or damaging the retracted nerve until after the surgery (generally referred to as a change in "nerve health" or "nerve status").

The present invention is directed at eliminating, or at least reducing the effects of, the above-described problems.

SUMMARY OF THE INVENTION

The present invention includes a system and methods capable of performing a variety of neurophysiologic assessments, and particularly nerve pathology monitoring (via Nerve Retractor mode), by combining neurophysiology monitoring with any of a variety of instruments used in or in preparation for surgery (referred to herein as "surgical accessories"). Other assessments performed by the system 10 may include one or more of, but not necessarily limited to, neuromuscular pathway status (Twitch Test), pedicle integrity testing (Screw Test), nerve proximity testing during surgical access (Detection), nerve pathology monitoring (Nerve Retractor), and detection of spontaneous muscle activity (Free Run EMG-which may be conducted alone or in conjunction with any other assessment). The nerve pathology monitoring of the present invention may be augmented by equipping a nerve root retractor with one or more pressure sensing technologies and/or providing an additional system or device for assessing or monitoring the pressure being exerted upon a nerve or nerve root before, during and/or after nerve retraction.

The fundamental method steps for performing the nerve pathology assessments (as well as many of the other assessments which may be performed) according to the present invention include: (a) stimulating one or more nerves with the surgical accessory (e.g. nerve retractor among others); (b) measuring the response of nerves innervated by the stimulation of step (a); (c) determining a relationship between the surgical accessory and the nerve based upon the response measured in step (b); and (d) communicating this relationship to the surgeon in an easy-to-interpret fashion.

The step of stimulating one or more nerves may be accomplished by applying any of a variety of suitable stimulation signals to an electrode(s) on the surgical accessory, including voltage and/or current pulses of varying magnitude and/or frequency. The stimulating step may be performed at different times depending upon the particular surgical accessory in question. For example, with regard to neural pathology monitoring, stimulation may be performed before, during and/or after retraction of the nerve root, regardless of whether additional pressure sensing features for monitoring the pressure being exerted upon a retracted nerve or nerve root are employed.

The step of measuring the response of nerves innervated by the stimulation step may be performed in any number of suitable fashions, including but not limited to the use of evoked muscle action potential (EMAP) monitoring techniques (that is, measuring the EMG responses of muscle groups associated with a particular nerve). According to one aspect of the present invention, the measuring step is preferably accomplished via monitoring or measuring the EMG responses of the muscles innervated by the stimulated nerve(s).

The step of determining a relationship between the surgical accessory and the nerve based upon the measurement step may be performed in any number of suitable fashions depending upon the manner of measuring the response, and may define the relationship in any of a variety of fashions (based on any number of suitable parameters and/or characteristics). By way of example, for neural pathology assessments according to the present invention, the relationship may be, by way of example only, whether the neurophysiologic response of the nerve has changed over time. Such changes may be quickly determined using a hunting algorithm to determine a stimulation threshold current level at various times during the procedure. According to one embodiment, these parameters may be augmented with information regarding the pressure being exerted upon a retracted nerve or nerve root.

The step of communicating this relationship to the surgeon in an easy-to-interpret fashion may be accomplished in any number of suitable fashions, including but not limited to the use of visual indicia (such as alpha-numeric characters, light-emitting elements, and/or graphics) and audio communications (such as a speaker element). By way of example, for nerve pathology monitoring, the determined threshold value may be visually displayed as a simple numerical value on the display. In addition, color coded graphics may be displayed to indicate the relative safety level indicated by the threshold value. When pressure sensing capabilities are added to the nerve root retractor according to one aspect of the present invention, the step of communicating the relationship to the user may also include information about the pressure being exerted upon a retracted nerve or nerve root, such as the retraction duration, the extent of retraction, and/or the resulting pressure.

The nerve pathology monitoring function of the present invention may be augmented with additional pressure sensing capabilities. This may be accomplished by positioning one or more pressure sensors on the nerve retractor and communicatively linking the pressure sensor to pressure mapping software on the control unit or other processor.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

The present invention is capable of performing a variety of neurophysiologic assessments, and particularly nerve pathology monitoring (via Nerve Retractor mode), by combining neurophysiology monitoring with any of a variety of instruments used in or in preparation for surgery (referred to herein as "surgical accessories"). Other assessments performed by the system 10 may include one or more of, but not necessarily limited to, neuromuscular pathway status (Twitch Test), pedicle integrity testing (Screw Test), nerve proximity testing during surgical access (Detection), and detection of spontaneous muscle activity (Free Run EMG-which may be conducted alone or in conjunction with any other mode). As will be described in greater detail below, the nerve pathology monitoring of the present invention may be augmented by equipping a nerve root retractor 29 with one or more pressure sensing technologies and/or providing an additional system or device for assessing or monitoring the pressure being exerted upon a nerve or nerve root before, during and/or after nerve retraction. It is expressly noted that, although described herein largely in terms of use in spinal surgery, the neuromonitoring system 10 and related methods of the present invention are suitable for use in any number of additional surgical procedures where neurological impairment due to nerve retraction is a concern.

Figure 1:
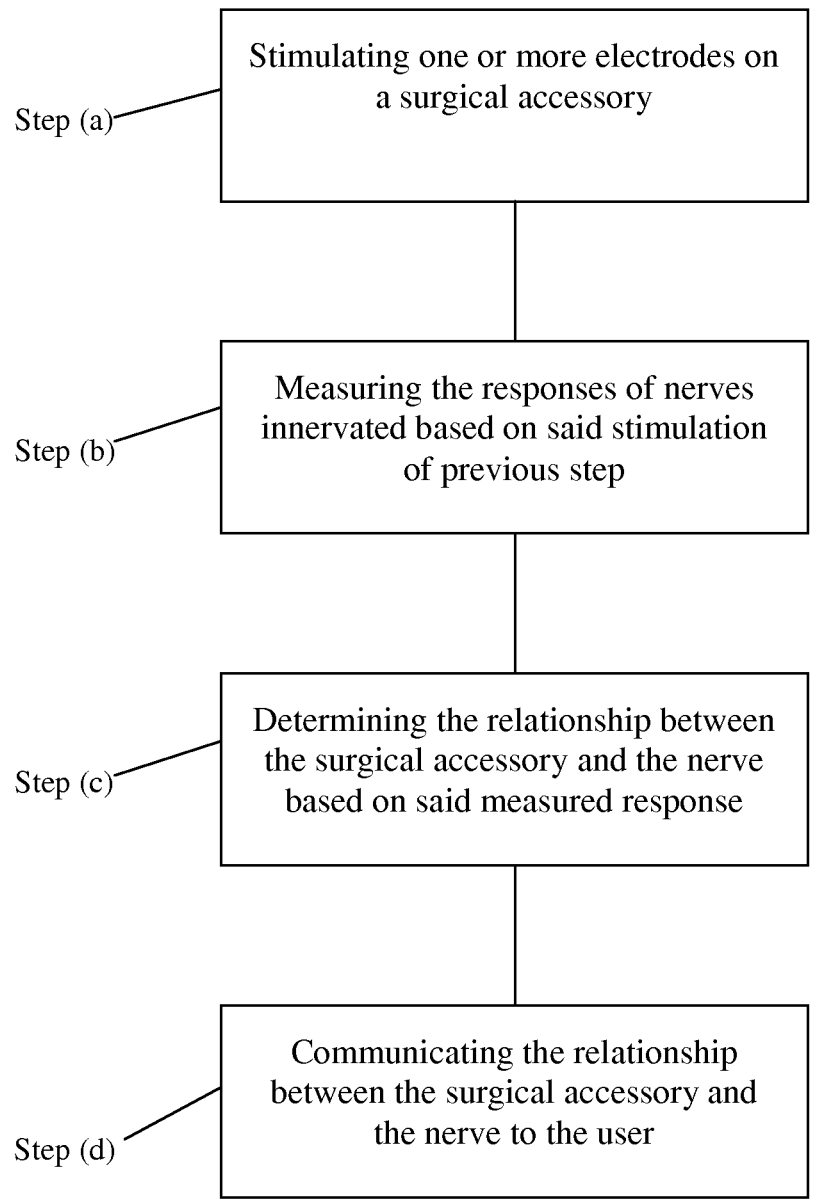
FIG. 1 is a flow chart illustrating the fundamental steps of the neurophysiology-based surgical system according to the present invention.

FIG. 1 illustrates the fundamental method steps for performing the nerve pathology assessments (as well as many of the other assessments which may be performed) according to the present invention, namely: (a) stimulating one or more nerves with the surgical accessory (e.g. nerve retactor); (b) measuring the response of nerves innervated by the stimulation of step (a); (c) determining a relationship between the surgical accessory and the nerve based upon the response measured in step (b); and (d) communicating this relationship to the surgeon in an easy-to-interpret fashion.

Figure 2:
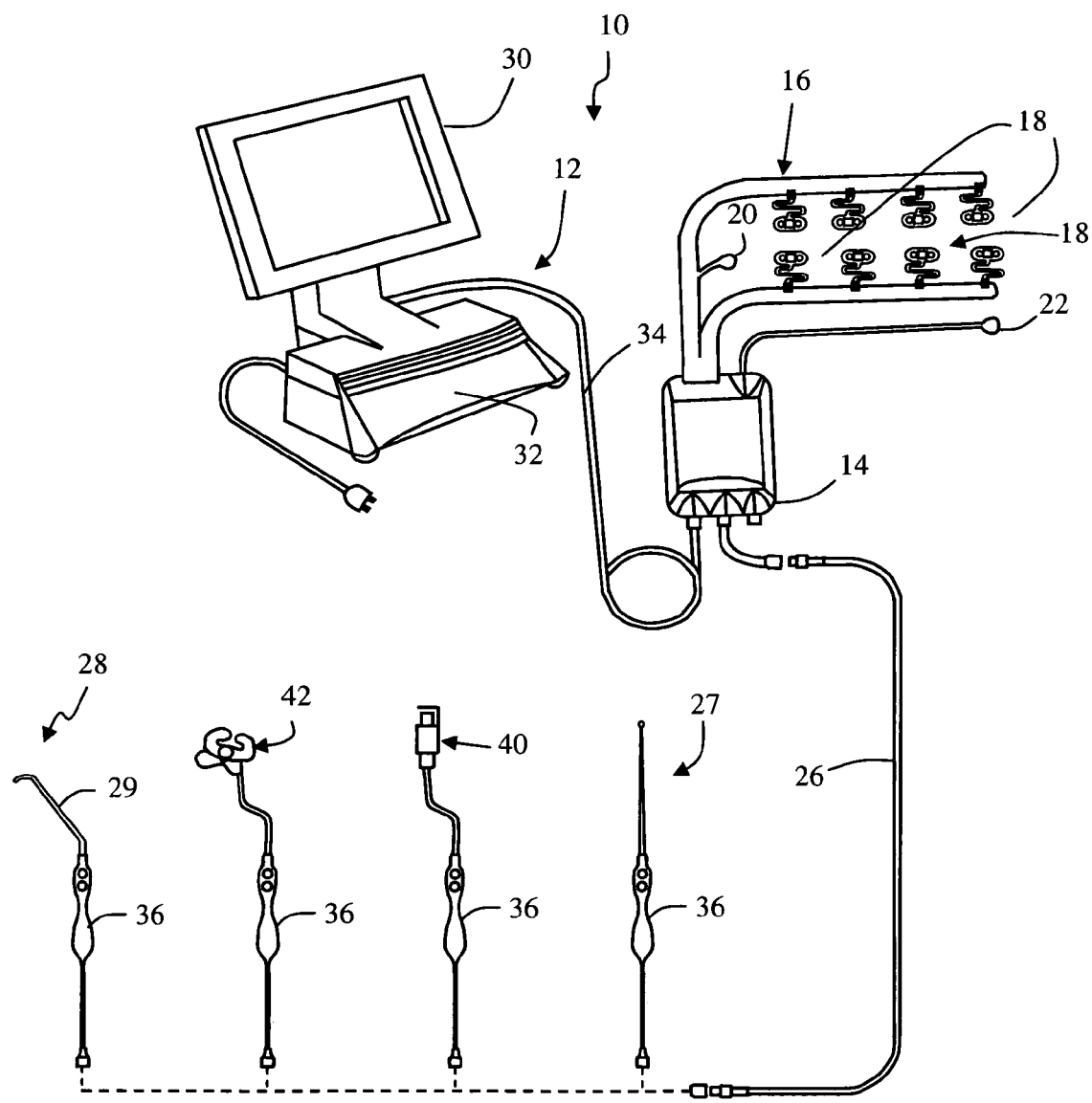
FIG. 2 is a perspective view of an exemplary system 10 capable of performing neurophysiologic assessments such as for example, detecting pedicle breaches, nerve proximity (detection), nerve pathology, neuromuscular pathway status, and spinal cord health.
Figure 3:
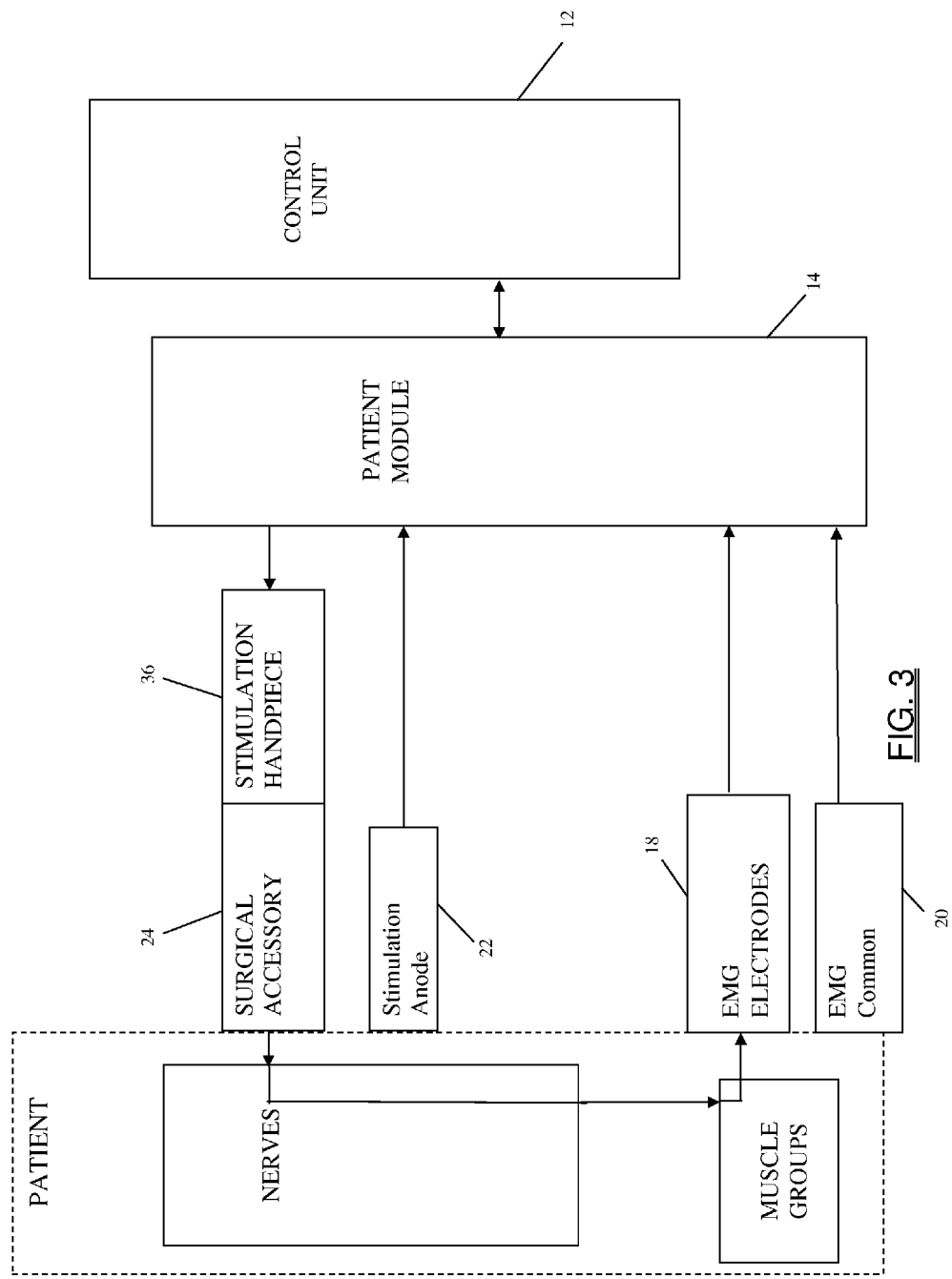
FIG. 3 is a block diagram of the system 10 shown in FIG. 2.

FIGS. 2-3 illustrate, by way of example only, a surgical system 10 provided in accordance with a broad aspect of the present invention. The surgical system 10 includes a control unit 12, a patient module 14, an EMG harness 16 including 8 pairs of EMG electrodes 18 and a return electrode 22 coupled to the patient module 14, and a host of surgical accessories 24 capable of being coupled to the patient module 14 via one or more accessory cables 26. In the embodiment shown, the surgical accessories 24 include (by way of example only) a screw test assembly 27 and a nerve root retractor assembly 28. Other surgical accessories not shown here may include, but are not necessarily limited to, a K-wire, a sequential dilation access system (e.g. dilating and working cannulae), taps, pedicle access probes, tissue retractor assemblies, and surface electrodes etc. . . . Additional components, such as for example an MEP stimulator (not shown) may also be connected to the system 10.

The control unit 12 includes a touch screen display 30 and a base 32, which collectively contain the essential processing capabilities for controlling the surgical system 10. The patient module 14 is connected to the control unit 12 via a data cable 34 (or optionally via wireless communication), which establishes the electrical connections and communications (digital and/or analog) between the control unit 12 and patient module 14. The main functions of the control unit 12 include receiving user commands via the touch screen display 30, activating stimulation in the selected mode (e.g. Nerve Retractor), processing signal data according to defined algorithms (described below), displaying received parameters and processed data, and monitoring system status and reporting fault conditions. The touch screen display 30 is preferably equipped with a graphical user interface (GUI) capable of communicating information to the user and receiving instructions from the user. The display 30 and/or base 32 may contain patient module interface circuitry that commands the stimulation sources, receives digitized signals and other information from the patient module 14, processes the EMG responses to extract characteristic information for each muscle group, and displays the processed data to the operator via the display 30.

The step (a) of stimulating one or more target tissues with the surgical accessory 24 is accomplished be coupling one or more surgical accessories 24 equipped with an electrode region(s) to a stimulation source (e.g. the patient module) communicatively linked to the control unit 12. Preferably, multiple coupling options are included with the system 10 to accommodate the variety of surgical accessories and functions performed by the system 10. By way of example only, a stimulation handpiece 36 (FIG. 1) may connect to the patient module 14 via an accessory cable 26 at one end, and couple a surgical accessory 24 (e.g. nerve retractor 29 thereby forming nerve retractor assembly 28; or a pedicle probe member-thereby forming screw test assembly 27) at the other end. The stimulation handpiece 36 may include one or more buttons 38 for selectively initiating stimulation according to the selected function. In a preferred embodiment the stimulation handpiece 36 is reusable and sterilizable. By way of further example only, an electric coupling device such as, by way of example only, stimulation clip 40 and/or stimulation clip 42 (FIG. 1) may be provided to couple surgical accessories 24 (such as for example, a tap member, access probe, tissue retractor assembly, and/or various cannulae) to the system 10 such that stimulation signals may be transmitted through the tool during use. The electric coupling device may be used alone or using in conjunction with stimulation handpiece 36, as is shown. Various other connectors may also be employed to couple the surgical accessory to the stimulation source, such as for example, a male/female type socket connection and other commonly know electrical connectors.

The step (b) of measuring the response of nerves innervated by the stimulation of step (a) may be performed in any number of suitable fashions, including but not limited to the use of evoked muscle action potential (EMAP) monitoring techniques (that is, measuring the EMG responses of muscle groups associated with a particular nerve). In a preferred embodiment, EMG response monitoring is accomplished via 8 pairs EMG electrodes 18 (placed on the skin over the muscle groups to be monitored), a common electrode 20 providing a ground reference to pre-amplifiers in the patient module 14, and an anode electrode 22 providing a return path for the stimulation current. A preferred EMG electrode for use with the system 10 is a dual surface electrode which is shown and described in detail in the commonly owned and co-pending U.S. patent application Ser. No. 11/048,404, entitled "Improved Electrode System and Related Methods," filed on Jan. 31, 2005, which is expressly incorporated by reference into this disclosure as if set forth in its entirety herein. It should be appreciated however, that any of a variety of known electrodes can be employed, including but not limited to surface pad electrodes and needle electrodes. It should also be appreciated that EMG electrode placement depends on a multitude of factors, including for example, the spinal cord level and particular nerves at risk and user preference, among others. In one embodiment (set forth by way of example only), the preferred EMG configuration is described for Lumbar surgery in Table 1, Thoracolumbar surgery in Table 2, and Cervical surgery in Table 3 below:

TABLE 1

Lumbar

| Color | Channel | Myotome | Nerve | Spinal Level |
| --- | --- | --- | --- | --- |
| Red | Right 1 | Right Vastus Medialis | Femoral | L2, L3, L4 |
| Orange | Right 2 | Right Tibialis Anterior | Common Peroneal | L4, L5 |
| Yellow | Right 3 | Right Biceps Femoris | Sciatic | L5, S1, S2 |
| Green | Right 4 | Right Medial Gastroc. | Post Tibial | S1, S2 |
| Blue | Left 1 | Left Vastus Medialis | Femoral | L2, L3, L4 |
| Violet | Left 2 | Left Tibialis Anterior | Common Peroneal | L4, L5 |
| Gray | Left 3 | Left Biceps Femoris | Sciatic | L5, S1, S2 |
| White | Left 4 | Left Medial Gastroc. | Post Tibial | S1, S2 |

TABLE 2

Thoracolumbar

| Color | Channel | Myotome | Nerve | Spinal Level |
| --- | --- | --- | --- | --- |
| Red | Right 1 | Right Abductor Pollicis Brevis | Median | C6, C7, C8, T1 |
| Orange | Right 2 | Right Vastus Medialis | Femoral | L2, L3, L4 |
| Yellow | Right 3 | Right Tibialis Anterior | Common Peroneal | L4, L5 |
| Green | Right 4 | Right Abductor Hallucis | Tibial | L4, L5, S1 |
| Blue | Left 1 | Left Abductor Pollicis Brevis | Median | C6, C7, C8, T1 |
| Violet | Left 2 | Left Vastus Medialis | Femoral | L2, L3, L4 |
| Gray | Left 3 | Left Tibialis Anterior | Common Peroneal | L4, L5 |
| White | Left 4 | Left Abductor Hallucis | Tibial | L4, L5, S1 |

TABLE 3

Cervical

| Color | Channel | Myotome | Nerve | Spinal Level |
| --- | --- | --- | --- | --- |
| Red | Right 1 | Right Deltoid | Axilliary | C5, C6 |
| Orange | Right 2 | Right Flexor Carpi Radialis | Median | C6, C7, C8 |
| Yellow | Right 3 | Right Abductor Pollicis Brevis | Median | C6, C7, C8, T1 |
| Green | Right 4 | Right Abductor Hallucis | Tibial | L4, L5, S1 |
| Blue | Left 1 | Left Deltoid | Axillary | C5, C6 |
| Violet | Left 2 | Left Flexor Carpi Radialis | Median | C6, C7, C8 |
| Gray | Left 3 | Left Abductor Pollicis Brevis | Median | C6, C7, C8, T1 |
| White | Left 4 | Left Abductor Hallucis | Tibial | L4, L5, S1 |

The step (c) of determining a relationship between the surgical accessory and the nerve based upon the response measured in step (b) may be performed in any number of suitable fashions depending upon the manner of measuring the response, and may define the relationship in any of a variety of fashions based on any number of suitable parameters and/or characteristics). By way of example only, the step of determining a relationship, within the context of a nerve pathology assessment, may involve identifying what stimulation current level is required to evoke a significant muscle response (i.e. the relationship between the surgical accessory (and more specifically the stimulation signal emitted from the surgical accessory) and the nerve may be defined as the stimulation threshold current level, described below).

Figure 4:
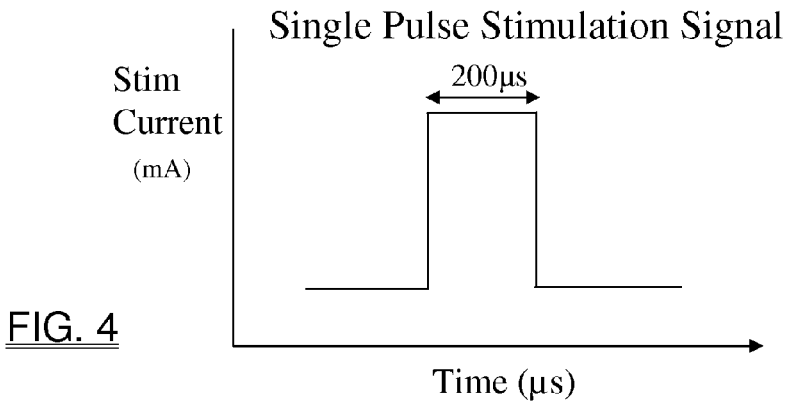
FIG. 4 is a graph illustrating an exemplary single pulse stimulation signal according to one embodiment of the present invention.
Figure 5:
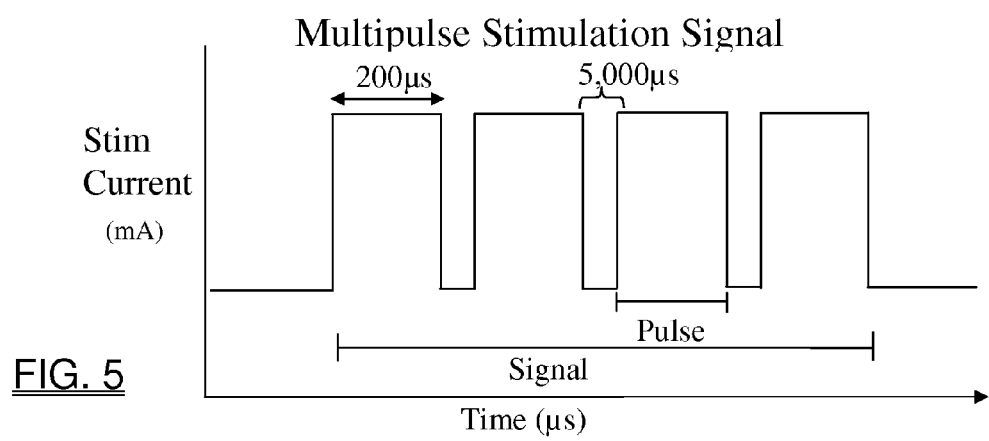
FIG. 5 is a is a graph illustrating an exemplary multipulse stimulation signal according to one embodiment of the present invention.
Figure 6:
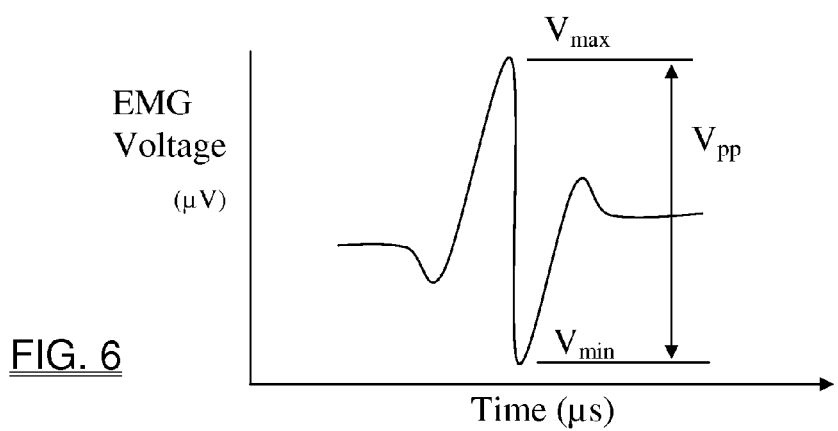
FIG. 6 is a graph illustrating an exemplary EMG response to the stimulus of FIG. 3 or 4.
Figure 7:
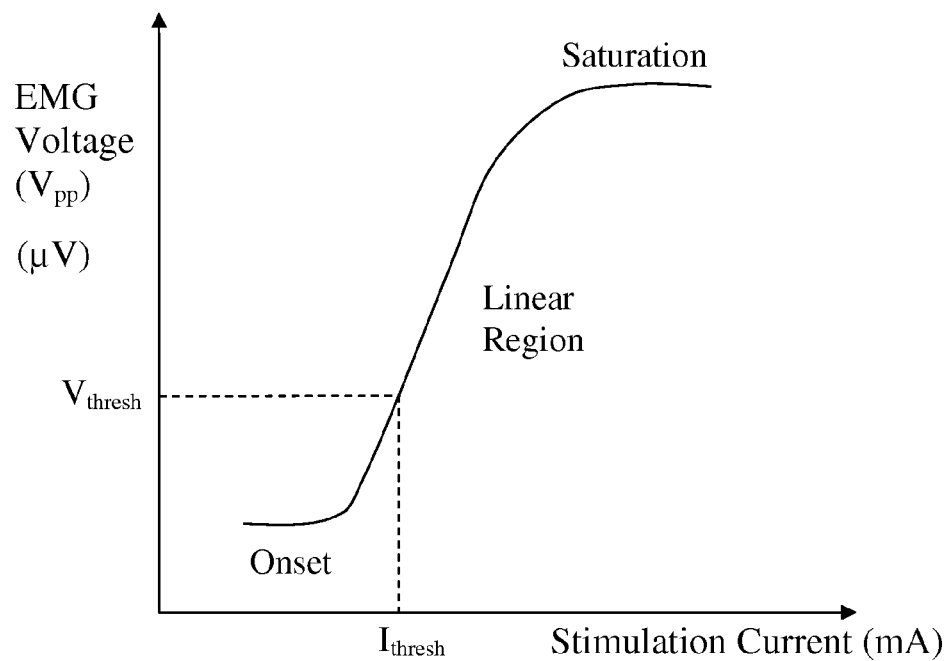
FIG. 7 is a graph illustrating a plot of peak-to-peak voltage (Vpp) for each given stimulation current level ($I_{Stim}$) forming a stimulation current pulse train according to the present invention (otherwise known as a "recruitment curve")

A basic premise underlying the methods employed by the system 10 for much of the neurophysiologic monitoring conducted is that neurons and nerves have characteristic threshold current levels ($I_{Thresh}$) at which they will depolarize, resulting in detectable muscle activity. Below this threshold current, stimulation signals, such as the single pulse signal shown by way of example only in FIG. 4 and the multi-pulse signal shown by way of example only in FIG. 5, will not evoke a significant EMG response. Each EMG response can be characterized by a peak-to-peak voltage of $V_{pp}=V_{max}-V_{min}$, shown in FIG. 6. Once the stimulation threshold ($I_{Thresh}$) is reached, the evoked response is reproducible and increases with increasing stimulation until saturation is reached as shown in FIG. 7. This is known as a "recruitment curve." In one embodiment, a significant EMG response is defined as having a $V_{pp}$ of approximately 100 uV. The lowest stimulation signal current, $I_{stim}$ that evokes this threshold voltage ($V_{Thresh}$) is called $I_{Thresh}$. Finding $I_{thresh}$ is useful in making neurophysiologic assessments because it provides a relative indication as to the degree of communication between a stimulation signal and nerve tissue. For example, as the degree of electrical communication between a stimulation signal and a nerve decreases, $I_{thresh}$ will increase. Conversely, as the degree of communication between the stimulation signal and a nerve increases, $I_{thresh}$ will decrease.

The system 10 capitalizes on and enhances the information derived from $I_{thresh}$ by quickly, accurately, and efficiently finding $I_{thresh}$ and comparing the determined value against predetermined safety indicator levels. Armed with the useful information conveyed by the system 10, the surgeon may detect early on any problem or potential problem and then act to avoid and/or mitigate the situation. By way of general example only, an excessively high $I_{thresh}$ or an increase over a previous $I_{thresh}$ measurement during Nerve Retractor mode may indicate a deterioration of nerve root function caused by excessive and/or prolonged retraction. On the opposite hand, a decrease in $I_{thresh}$ over previous measurements may indicate During Screw Test and Detection modes, a low $I_{thresh}$ value may indicate a breach in the pedicle, or the close proximity of a nerve, respectively.

To quickly determine $I_{thresh}$, the system 10 may employ a variety of suitable algorithms and techniques which are described in detail in the "NeuroVision Applications," all of which are incorporated by reference below, as if they were set forth herein in their entireties. One exemplary threshold hunting algorithm is described hereafter in only brief detail. The threshold hunting algorithm utilizes a bracketing method and a bisection method to find $I_{thresh}$. The bracketing method finds a range (bracket) of stimulation currents that must contain $I_{thresh}$. To accomplish this, the algorithm directs stimulation to begin at a predetermined current level (based on the selected function). For each subsequent stimulation, the current level is doubled from the previous current level. This doubling continues until a until a stimulation current recruits, that is, results in an EMG response with a $V_{pp}$ greater or equal to $V_{thresh}$ (e.g. 100 uV). This first stimulation current to recruit, together with the last stimulation current to have not recruited, forms the initial bracket. If the stimulation current threshold, $I_{thresh}$ of a channel exceeds a maximum stimulation current, that threshold is considered out of range.

After the bracket containing the threshold current $I_{thresh}$ has been determined, the initial bracket is successively reduced via the bisection method to a predetermined width. This is accomplished by applying a first bisection stimulation current that bisects (i.e. forms the midpoint of) the initial bracket. If this first bisection stimulation current recruits, the bracket is reduced to the lower half of the initial bracket. If this first bisection stimulation current does not recruit, the bracket is reduced to the upper half of the initial bracket. This process is continued for each successive bracket until $I_{thresh}$ is bracketed by stimulation currents separated by the predetermined width. In one embodiment, the midpoint of this final bracket may be defined as $I_{thresh}$; however, any value falling within the final bracket may be selected as $I_{thresh}$ without departing from the scope of the present invention.

During some functions (e.g. Screw Tests and Detection) stimulations may stop after $I_{thresh}$ is determined for the channel possessing the lowest $I_{thresh}$. For other functions (e.g. Nerve Retractor), however, it may useful to determine $I_{thresh}$ for every channel. To accomplish this quickly, the hunting algorithm may employ additional methods allowing it to omit certain stimulations, thereby reducing the number of stimulations and time required to obtain an $I_{thresh}$ value on each channel. $I_{thresh}$ is still found using the bracketing and bisection methods described above, however the algorithm will omit stimulations for which the result is predictable from data previously acquired. When a stimulation signal is omitted, the algorithm proceeds as if the stimulation had taken place. This permits the algorithm to proceed to the next required stimulation immediately, without a time delay inherently associated with each stimulation signal. To further reduce the number of stimulations required over the time frame of an entire surgical procedure, the algorithm may confirm previously obtained $I_{thresh}$ values (e.g. by stimulation at current levels just below and at/or just above $I_{thresh}$ and determining whether the resulting responses are consistent with the previously acquired $I_{thresh}$ value), rather than initiating stimulations from the beginning each time a function is performed.

The final step (d) of communicating this relationship to the surgeon in an easy-to-interpret fashion may be accomplished in any number of suitable fashions, including but not limited to the use of visual indicia (such as alpha-numeric characters, light-emitting elements, and/or graphics) and audio communications (such as a speaker element). By way of example only, the determined $I_{thresh}$ value may be visually displayed as a simple numerical value on display 30. In addition, color coded graphics may be displayed to indicate the relative safety level indicated by the $I_{thresh}$ (e.g. "green" for a range of stimulation thresholds below (or above, depending on the selected mode) a predetermined safe value, "red" for a range of stimulation thresholds above (or below, depending on the mode) a predetermined unsafe value, and "yellow" for the range of stimulation thresholds in between the predetermined safe and unsafe values—designating caution). When pressure sensing capabilities are added to the nerve root retractor according to one aspect of the present invention, the step of communicating the relationship to the user may also include information about the pressure being exerted upon a retracted nerve or nerve root, such as the retraction duration, the extent of retraction, and/or the resulting pressure. In one embodiment, set forth by way of example only, the information shown on the display 30 may include at least some of the following components (depending on the active mode) as set forth in Table 1:

reference as if set forth fully herein. The Basic Screw Test, Difference Screw Test, and Dynamic Screw Test modes are designed to assess the integrity of bone (e.g. pedicle) during all aspects of pilot hole formation (e.g., via an awl), pilot hole preparation (e.g. via a tap), and screw introduction (during and after). These modes are described in greater detail in Int'l Patent App. No. PCT/US02/35047 entitled "System and Methods for Performing Percutaneous Pedicle Integrity Assessments," filed on Oct. 30, 2002, and PCT/US2004/025550, entitled "System and Methods for Performing Dynamic Pedicle Integrity Assessments," filed on Aug. 5, 2004 the entire contents of which are both hereby incorporated by reference as if set forth fully herein. The MaXcess® Detection mode is designed to detect the presence of nerves during the use of the various surgical access instruments of the neuromonitoring system 10, including the k-wire 62, dilator 64, cannula 66, retractor assembly 70. This mode is described in greater detail within Int'l Patent App. No PCT/US02/22247, entitled "System and Methods for Determining Nerve Proximity, Direction, and Pathology During Surgery," filed on Jul. 11, 2002, the entire contents of which is hereby

TABLE 1

| Screen Component | Description |
| --- | --- |
| Spine Image | An image of the human body/skeleton showing the electrode placement on the body, with labeled channel number tabs on each side (1-4 on the left and right). Left and right labels will show the patient orientation. The channel number tabs may be highlighted or colored depending on the specific function being performed. |
| Myotome & Level Names | A label to indicate the Myotome name and corresponding Spinal Level(s) associated with the channel of interest. |
| Menu | A drop down navigation component for toggling between functions. |
| Display Area | Shows procedure-specific information including stimulation results. |
| Color Indication | Enhances stimulation results with a color display of green, yellow, or red corresponding to the relative safety level determined by the system. |
| Mode Indicator | Graphics and/or name to indicate the currently active mode (Twitch Test, Free-Run EMG, Basic Screw Test, Dynamic Screw Test, Difference Screw Test, Detection, Nerve Retractor). In an alternate embodiment, Graphics and/or name may also be displayed to indicate the instrument in use, such as the dilator, K-wire, retractor blades, screw test instruments, and associated size information, if applicable, of the cannula, with the numeric size. If no instrument is in use, then no indicator is displayed. |
| Stimulation Bar | A graphical stimulation indicator depicting the present stimulation status (i.e. on or off and stimulation current level) |
| Sequence Bar | Shows the last seven stimulation results and provides for annotation of results. |
| EMG waveforms | EMG waveforms may be optionally displayed on screen along with the stimulation results. |
| Pressure Indicia | Data regarding pressure being exerted upon a retracted nerve or nerve root, such as the duration of retraction, the extent of retraction, and/or the resulting pressure. |

By way of example only, the various functional modes capable of being performed by system 10 may include, but is not necessarily limited to, the Twitch Test, Free-run EMG, Basic Screw Test, Difference Screw Test, Dynamic Screw Test, MaXcess® Detection, Nerve Retractor, MEP Auto, MEP manual, and SSEP modes, all of which are described only briefly hereafter. The Twitch Test mode is designed to assess the neuromuscular pathway via the so-called "train-of-four test" test to ensure the neuromuscular pathway is free from muscle relaxants prior to performing neurophysiology-based testing, such as bone integrity (e.g. pedicle) testing, nerve detection, and nerve retraction. This is described in greater detail within Int'l Patent App. No. PCT/US2005/036089, entitled "System and Methods for Assessing the Neuromuscular Pathway Prior to Nerve Testing," filed Oct. 7, 2005, the entire contents of which is hereby incorporated by incorporated by reference as if set forth fully herein. The MEP Auto and MEP Manual modes are designed to test the motor pathway to detect potential damage to the spinal cord by stimulating the motor cortex in the brain and recording the resulting EMG response of various muscles in the upper and lower extremities. The SSEP function is designed to test the sensory pathway to detect potential damage to the spinal cord by stimulating peripheral nerves inferior to the target spinal level and recording the action potential from sensors superior to the spinal level. The MEP Auto, MEP manual, and SSEP modes are described in greater detail within Int'l Patent App. No. PCT/US2006/003966, entitled "System and Methods for Performing Neurophysiologic Assessments During Spine Surgery," filed on Feb. 2, 2006, the entire contents of which is hereby incorporated by reference as if set forth fully herein. The Nerve Retractor mode is designed to assess the health or pathology of a nerve before, during, and after retraction of the nerve during a surgical procedure. This mode is described in greater detail within Int'l Patent App. No. PCT/US02/30617, entitled "System and Methods for Performing Surgical Procedures and Assessments," filed on Sep. 25, 2002, the entire contents of which is hereby incorporated by reference as if set forth fully herein.

Nerve pathology monitoring as it may be performed by the system 10 during Nerve Retractor mode is described hereafter in more detail. The system 10 preferably accomplishes neural pathology monitoring via the Nerve Retractor mode, specifically by determining a baseline stimulation threshold (again, stimulation threshold is the value $I_{thresh}$) with direct contact between the nerve retractor 29 and the nerve, prior to retraction. Subsequent stimulation thresholds are determined during retraction and they are compared to the baseline threshold. Significant changes in the stimulation threshold may indicate potential trauma to the nerve caused by the retraction and are displayed to the user on the display 30. An increase in $I_{thresh}$ over time is an indication that the nerve function is deteriorating. By monitoring this the surgeon may intra-operatively assess if the retracted nerve is being damaged or otherwise compromised (such as due to a prolonged surgery), such that it can be temporarily released to allow it to recover before returning to retraction to continue with the surgery. It's believed that releasing the nerve root in this fashion will prevent or reduce the adverse effects (nerve function compromise) that may otherwise result from prolonged retraction. Changes in $I_{thresh}$ in the opposite direction (i.e. decreases in $I_{thresh}$ over time) may indicate that the surgical procedure is improving or aiding a previously unhealthy nerve, such as during spinal decompression surgery. For accurate and timely information, $I_{thresh}$ may preferably be determined for each channel according to the multi-channel hunting algorithm described above.

Figure 8:
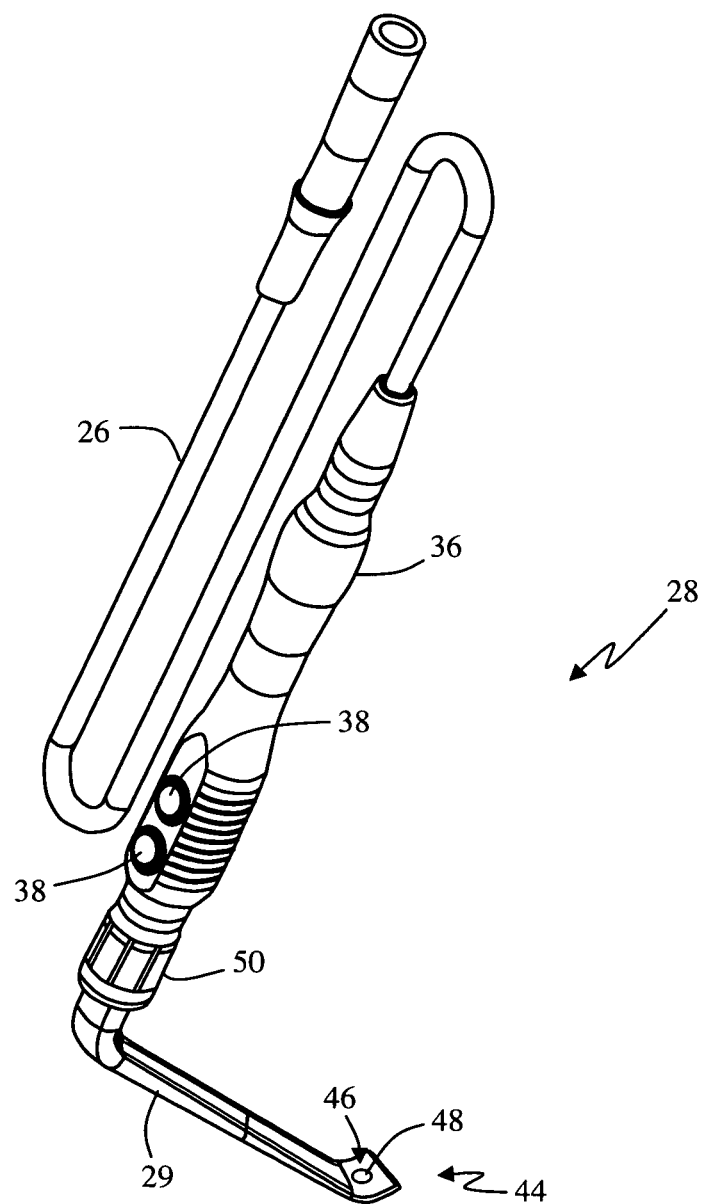
FIGS. 8-9 are perspective and side views, respectively, of an exemplary nerve root retractor assembly according to one embodiment of the present invention.
Figure 9:
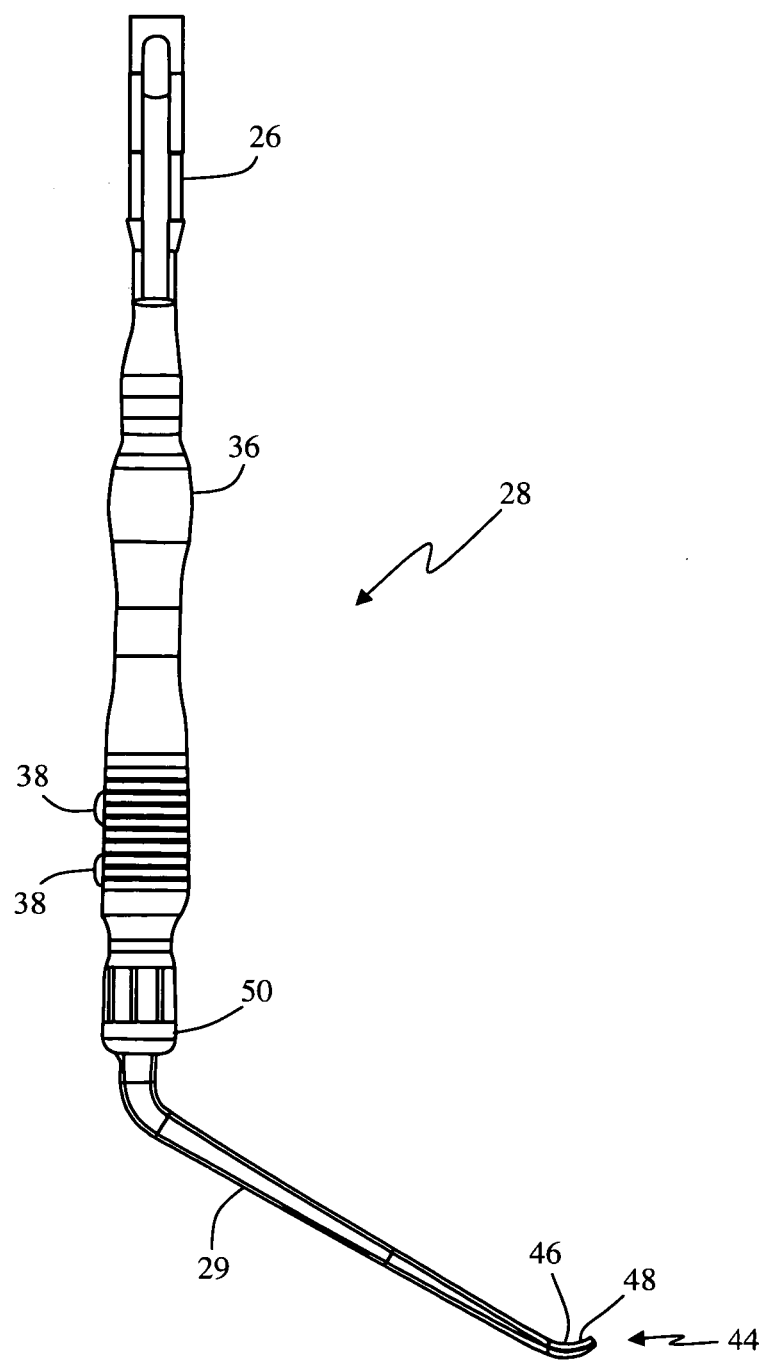
Figure 10:
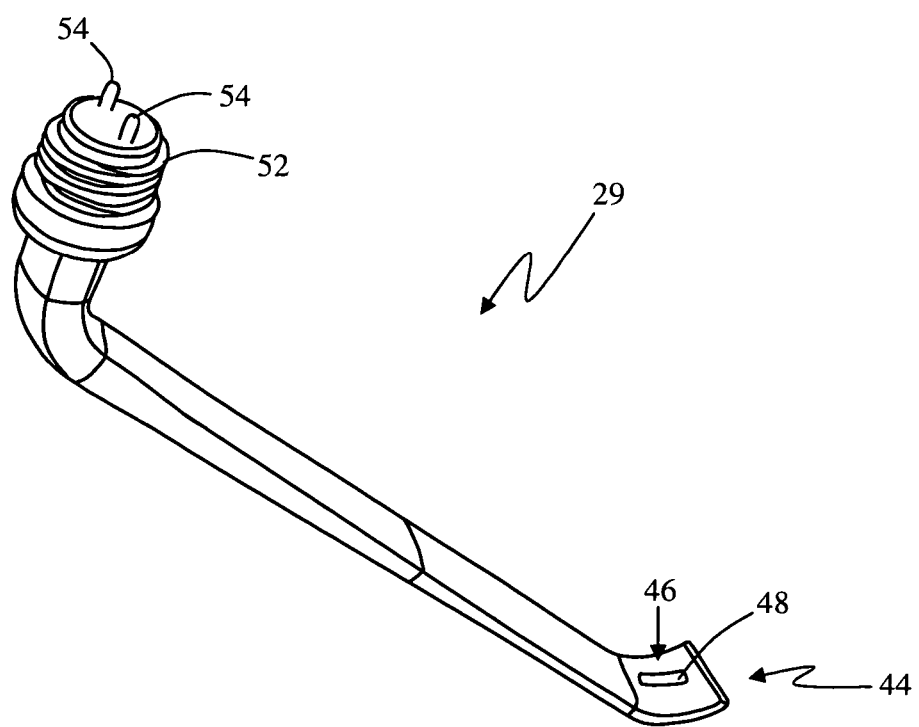
FIG. 10 is a perspective view of an exemplary nerve root retractor forming part of the assembly of FIGS. 8 and 9, according to one embodiment of the present invention.

The nerve root retractor assembly 28, shown in a preferred embodiment in FIGS. 8-10, comprises the stimulation handpiece 36 employed with a selectively removable nerve root retractor 29. The nerve root retractor 29 has a generally angled orientation relative to the longitudinal axis of the stimulation handpiece 36. The distal end 44 is generally curved and includes an arcuate nerve engagement surface 46 equipped with, by way of example only, at least one stimulation electrode 48. As best shown in FIG. 10, the nerve root retractor 29 is preferably removable from the stimulation handpiece 36. To accomplish this, the stimulation handpiece 36 includes a detachable cap member 50. Threads 52 are provided on the proximal end of the nerve root retractor 29 to allow a threaded coupling engagement between the stimulation handpiece 36 and the nerve root retractor 29. During such engagement, electrical contacts 54 on the nerve root retractor 29 become electrically coupled to the stimulation handpiece 36 such that, upon activation of one or more of the buttons 38 a stimulation current signal will be transmitted from the control unit 12 and/or patient module 14 and delivered to the stimulation electrode(s) 48 on the nerve root retractor 29 for the purpose of performing neural pathology monitoring according to the present invention. The nerve root retractor 29 is preferably disposable and, as described above, the stimulation handpiece 36 is preferably reusable and sterilizable. It should be understood that while the nerve retractor 29 is shown primarily in use with the stimulation handpiece 36 to form nerve retractor assembly 28, nerve retractor 29 may be used with any suitable handle and/or may include a fixed handle. When nerve retractor 29 is used without stimulation handpiece 36 it may be coupled to the system 10 via one of the electric coupling devices 40, 42, a male/female type electrical coupler, or any other form of electric coupling.

In use, the nerve root retractor 29 is introduced into or near a surgical target site in order to hook and retract a given nerve out of the way. According to the present invention, the nerve root may be stimulated (monopolar or bipolar) before, during, and/or after retraction in order to assess the degree to which such retraction impairs or otherwise degrades nerve function over time. To do so, the user may operate one or more buttons 38 of the stimulation handpiece 36 to selectively transmit a stimulation current signal, according to the algorithm described above, from the patient module 14 to the electrode(s) 48 on the engagement surface 46 of the nerve root retractor 29. By monitoring the myotome(s) associated with the nerve root being retracted (via the EMG harness 16) and assessing the resulting EMG responses to preferably determine $I_{thresh}$ (via the control unit 12), the system 10 can assess whether (and the degree to which) such retraction impairs or adversely affects nerve function over time. With this information, a user may wish to periodically release the nerve root from retraction to allow nerve function to recover, thereby preventing or minimizing the risk of long-term or irreversible nerve impairment. Similarly, an unhealthy nerve may be monitored in the same manner to determine if nerve function improves due to a particular procedure, such as spinal nerve decompression surgery.

Figure 11:
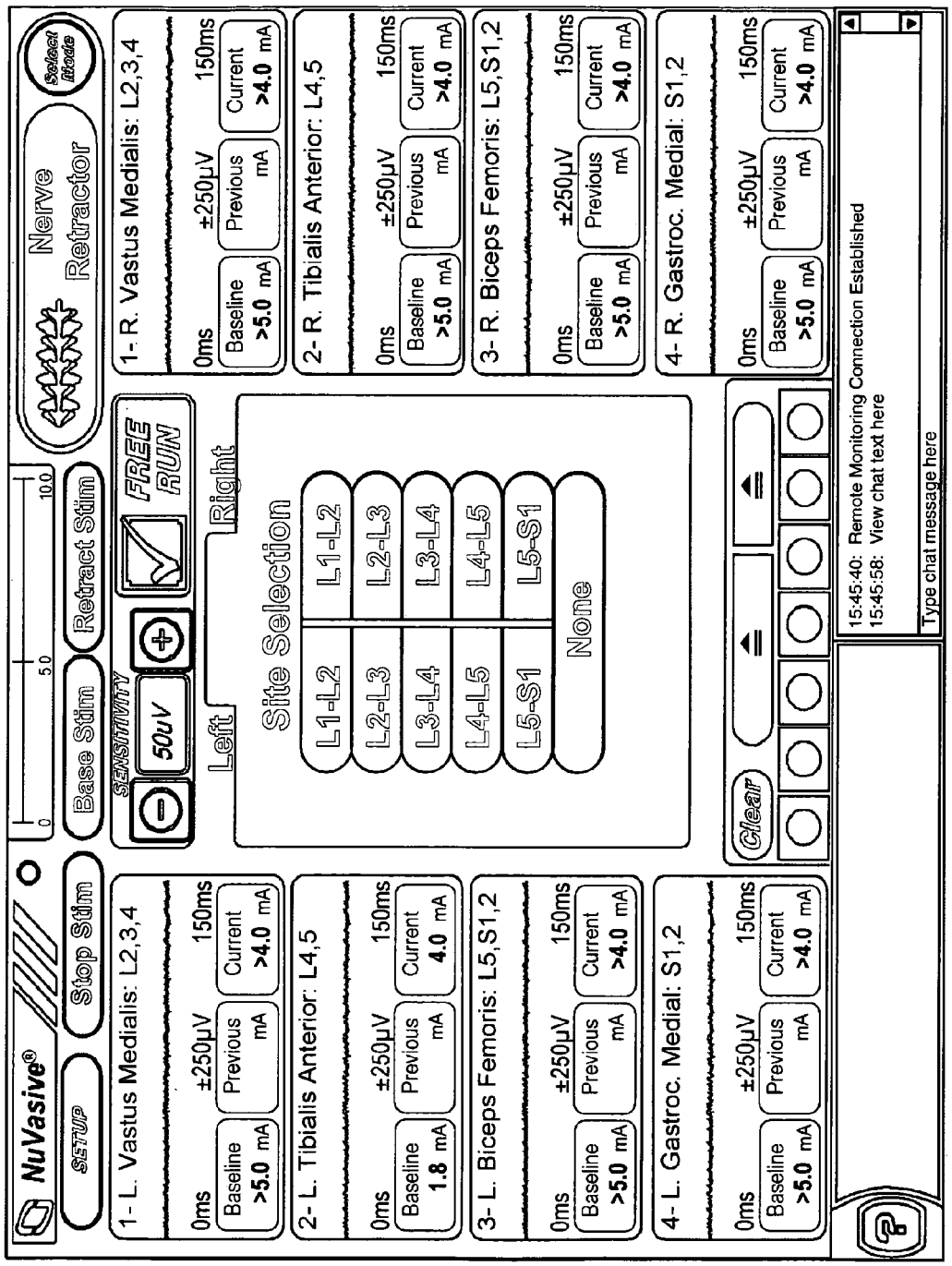
FIG. 11 is an exemplary screen display illustrating one embodiment of the Nerve Retractor mode for performing neural pathology monitoring according to one embodiment of the present invention.

The nerve retraction monitoring feature of the present invention is best viewed with regard to FIG. 11. The screen display for the Nerve Retractor mode may include any of a variety of indicia capable of communicating parameters associated with the nerve retraction monitoring feature of the present invention to a surgeon, including but not limited to, channel windows containing one or more of the channel number, myotome name, spinal level, baseline $I_{thresh}$, previous $I_{thresh}$, current $I_{thresh}$ and the associated waveform, and various selection tabs for one or more of starting baseline stimulation, starting retraction stimulation, stopping stimulation, activating free-run EMG monitoring and adjusting the sensitivity of the free-run EMG, noting the retraction site, mode selection, annotating results, and remote messaging.

As described above, the nerve pathology assessments (Nerve Retractor mode) conducted by the system 10 may be further augmented via the use of any number of pressure sensing technologies working in addition to the stimulation based nerve monitoring described above and throughout this disclosure. The pressure sensing features contemplated herein offer added safety and qualitative assessment features by providing the ability to monitor how much pressure is being applied to a particular nerve during nerve root retraction. This pressure may be a function of, among other factors, the degree of retraction (that is, distance the nerve is moved during retraction) and the duration of retraction. In any case, the pressure resulting on a nerve during retraction—if too high in magnitude and/or too long in duration—may result in neurologic deficit of varying degrees. By monitoring the pressure according to the present invention, a user may selectively reduce the degree of retraction (such as by moving the retractor assembly 28 and nerve closer to the "natural" position of the nerve) and/or periodically releaseing the nerve to avoid and/or minimize any resulting neurologic deficit due to retraction.

The pressure sensing technologies may include any number of commercially available and/or publicly known pressure sensing technologies, and/or those later developed. The commercially available and/or publicly known pressure sensing technologies include, but are not necessarily limited to, the piezoelectric-based pressure sensing technique shown and described in U.S. Pat. No. 5,769,781 to James Chappuis, the capacitive-based pressure mapping system shown and described in U.S. Pat. No. 5,010,772 to Bourland et. al., the strain gauge-based pressure sensing technology shown and described in U.S. Pat. No. 4,784,150 to Voorhies et. al., the pressure sensitive ink-based technique shown and described in U.S. Pat. No. 5,989,700 to Krivopal, and that shown and described in U.S. Pat. No. 6,272,936 to Oreper et. al.

Figure 12:
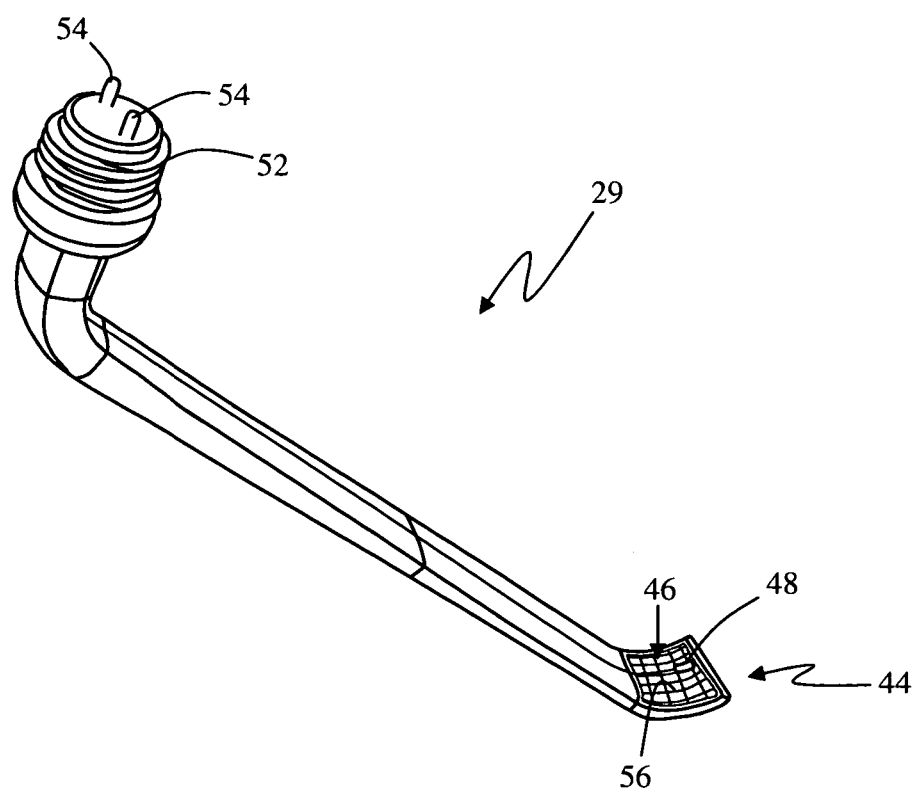
FIG. 12 is a perspective view of an exemplary nerve root retractor including a pressure sensor according to one embodiment of the present invention.

Augmenting the nerve pathology monitoring with pressure sensing capabilities may be accomplished in any number of suitable manners, including but not limited to equipping the nerve retractor assembly 28 (and more specifically, one or more of the nerve root retractor 29, the stimulation handpiece 36, the distal end 44, and the nerve engagement surface 46) with one or more pressure sensing technologies. By way of example only, with reference to FIG. 9, this may be done by equipping the nerve engagement surface 46 with a pressure sensor 56. By way of example only, the pressure sensor 56 illustrated in FIG. 12 is a capacitive foam grid (comprising any number of suitable grid units) adhered to nerve engagement surface 46 of nerve retractor 29. While pressure sensor 56 is shown herein having a small number of relatively large grid units, this is done for illustrative purposes. It will be readily understood by those skilled in the art that that any number of grid units and unit sizes may be utilized, and sensor 56 preferably comprises a large number of relatively small grid units to increase precision. To communicatively link the pressure sensor 56 to a processor unit, a data cable (not shown) may be run along the nerve retractor 29, and is preferably integrated within the interior of nerve retractor 29, and from there may be connected to the processing unit via cable 58. Alternatively, wireless communication may be used to link the pressure sensor and processing unit. As will be discussed below, the processor may be control unit 12 or an additional dedicated processor may be employed for pressure sensing features. In use, pressure applied to the capacitive foam grid induces voltage responses corresponding to the affected grid units. The voltage responses are relayed to the processor which translates the response into one or more of numerical and/or graphical (e.g. color) indicia relating to pressure, which may be displayed to the surgeon.

According to a further embodiment of the present invention, a separate system or device may be employed for assessing or monitoring the pressure being exerted upon a nerve or nerve root before, during and/or after nerve retraction. Such a separate system may supplant (that is, take the place of) and/or augment (that is, serve in along with) the nerve root retractor 29 equipped with pressure sensing capabilities described above.

Figure 13:
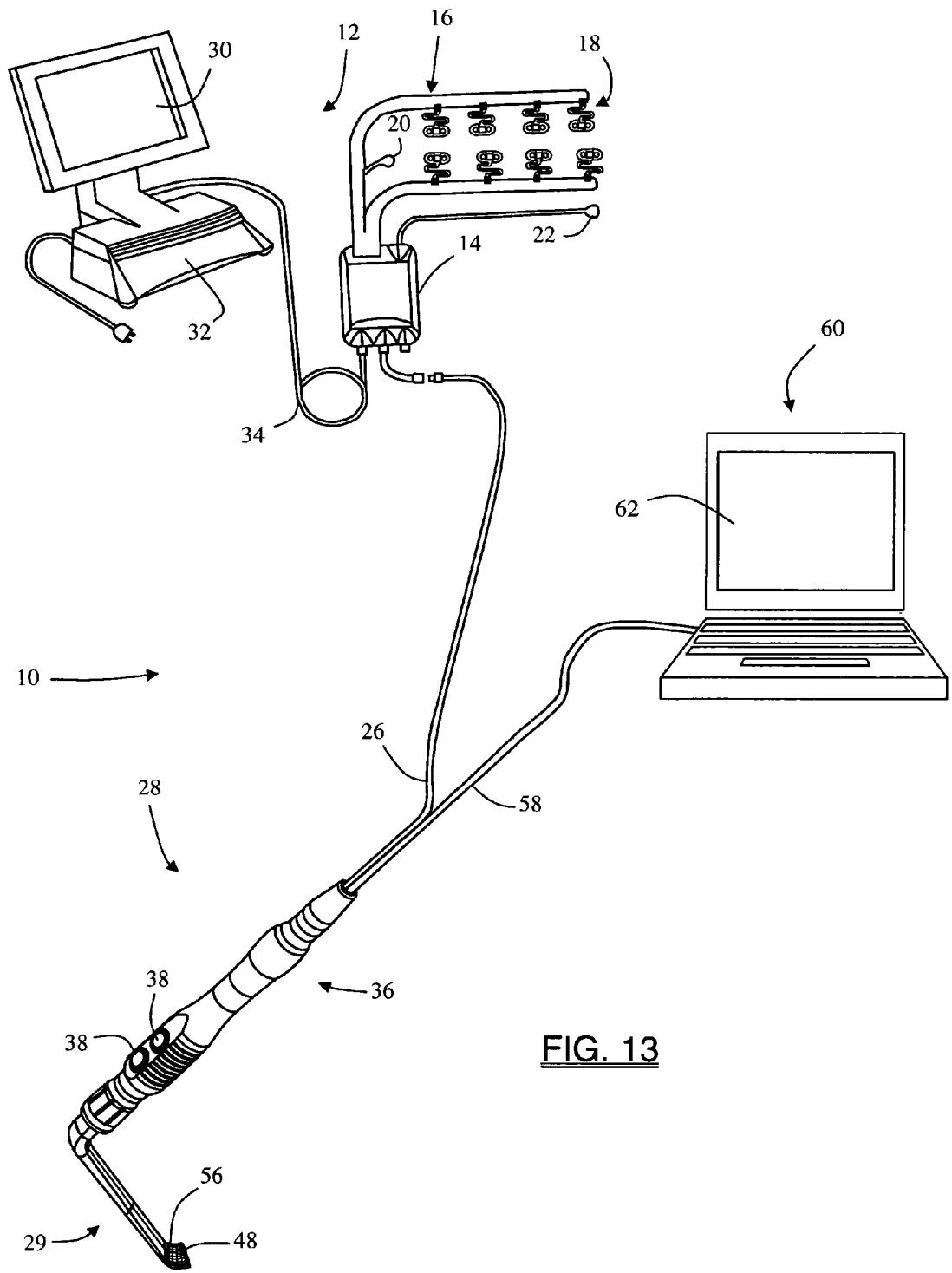
FIG. 13 is a perspective view of the system of FIG. 2 adapted to perform additional pressure sensing functions according to one embodiment of the present invention.

With reference to FIG. 13, according to one embodiment, set forth by way of example only, the pressure sensing features of the system 10 are controlled via a separate processing unit 60 while the EMG based nerve monitoring features are controlled via control unit 12 (as described throughout the description). Processing unit 60 is preferably a personal workstation or laptop computer (by way of example only) running pressure sensing software designed to interface with the pressure sensor 56 and display pressure data to the user on the processor screen 62. One such software program, by way of example only, is the X3 Series software distributed by XSENSOR™ Technology Corporation, Calgary Canada. In use, processing unit 60 is preferably arranged near the control unit 12 such that the surgeon may view nerve pathology data from the display 30 and pressure data from screen 62 at the same time.

Figure 14:
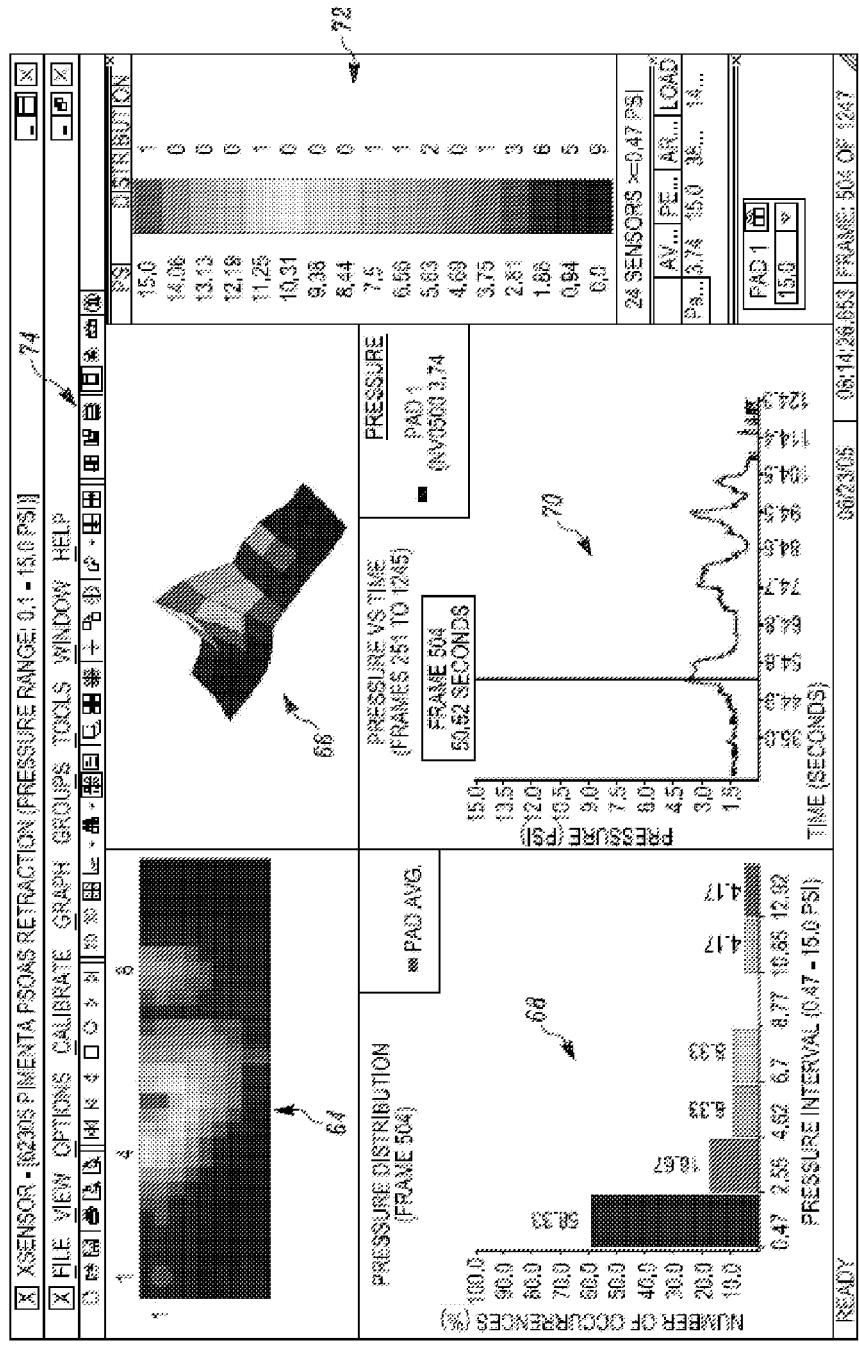
FIG. 14 is an exemplary multi-function screen display of the pressure sensing features of the system 10 according to one embodiment of the present invention.

As previously mentioned, pressure applied to the retracted nerve may be a function of, among other factors, the degree of retraction (that is, distance the nerve is moved during retraction) and the duration of retraction, either of which may result in neurologic deficit of varying degrees. With reference to FIG. 14, various pressure mapping features of the present embodiment that allow the surgeon to asses both the extent and duration of pressure applied to the retracted nerve are illustrated. FIG. 14 illustrates by way of example, a multi-function screen view of the pressure sensing software. The multi-function screen may include (by way of example only) a 2-dimensional (2-D) grid map 64, a 3-dimensional (3-D) grid map 66, and a pressure distribution chart 68, and a pressure vs. time (PvT) chart 70, a legend 72, and a tool bar 74. The tool bar 74 and legend 72 may be found on all screen views of the pressure mapping software. The tool bar 74 allows the user to select between different view screens, among other functions (such as for example, selecting the desired sensor range and precision). The legend 74 indicates the numerical pressure value associated with a specific color (e.g. in one example red indicates the highest pressure of the selected range, 15.0 PSI in FIG. 14).

Figure 15:
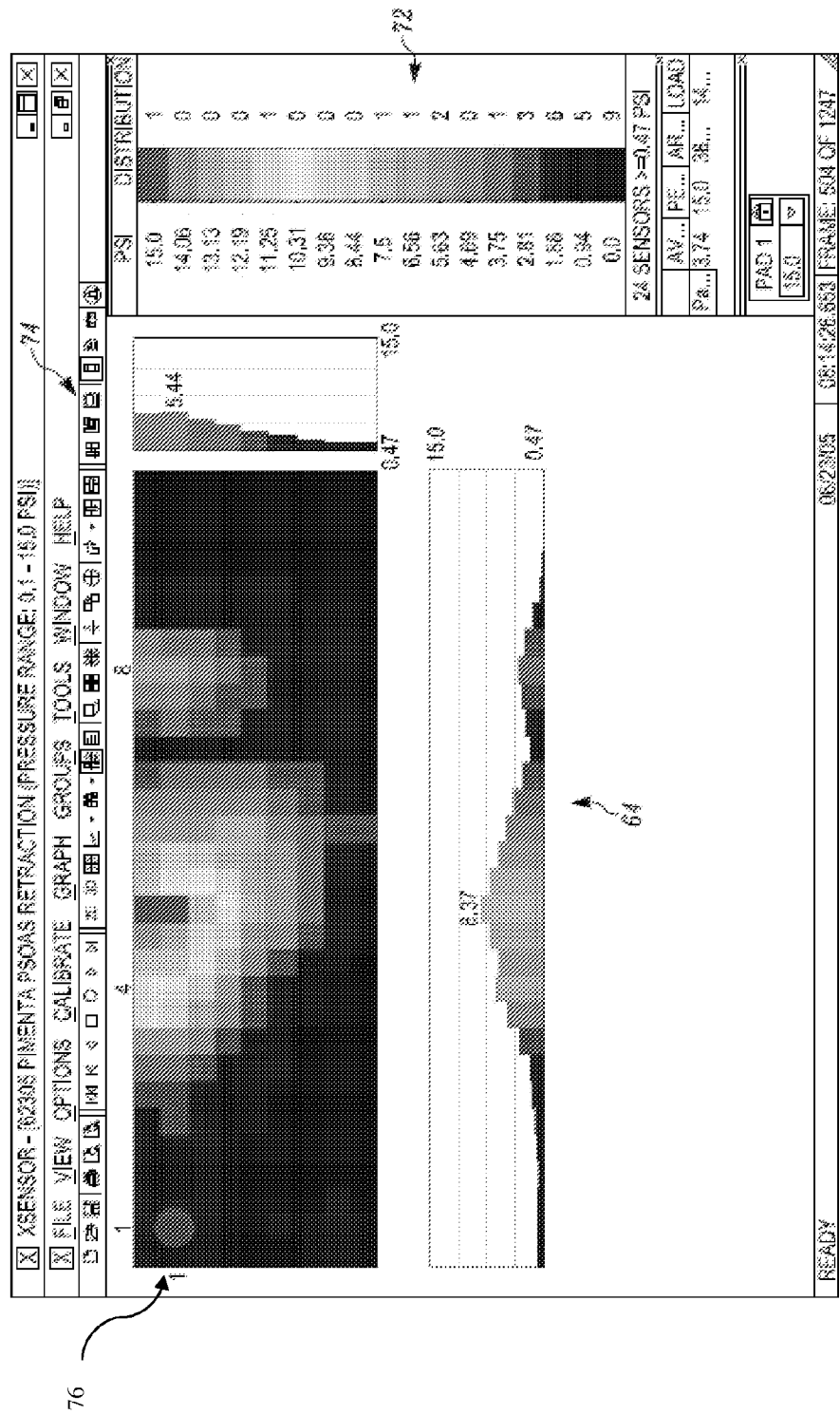
FIG. 15 is an exemplary full screen display of the 2-dimensional pressure mapping feature according to one embodiment of the present invention.
Figure 16:
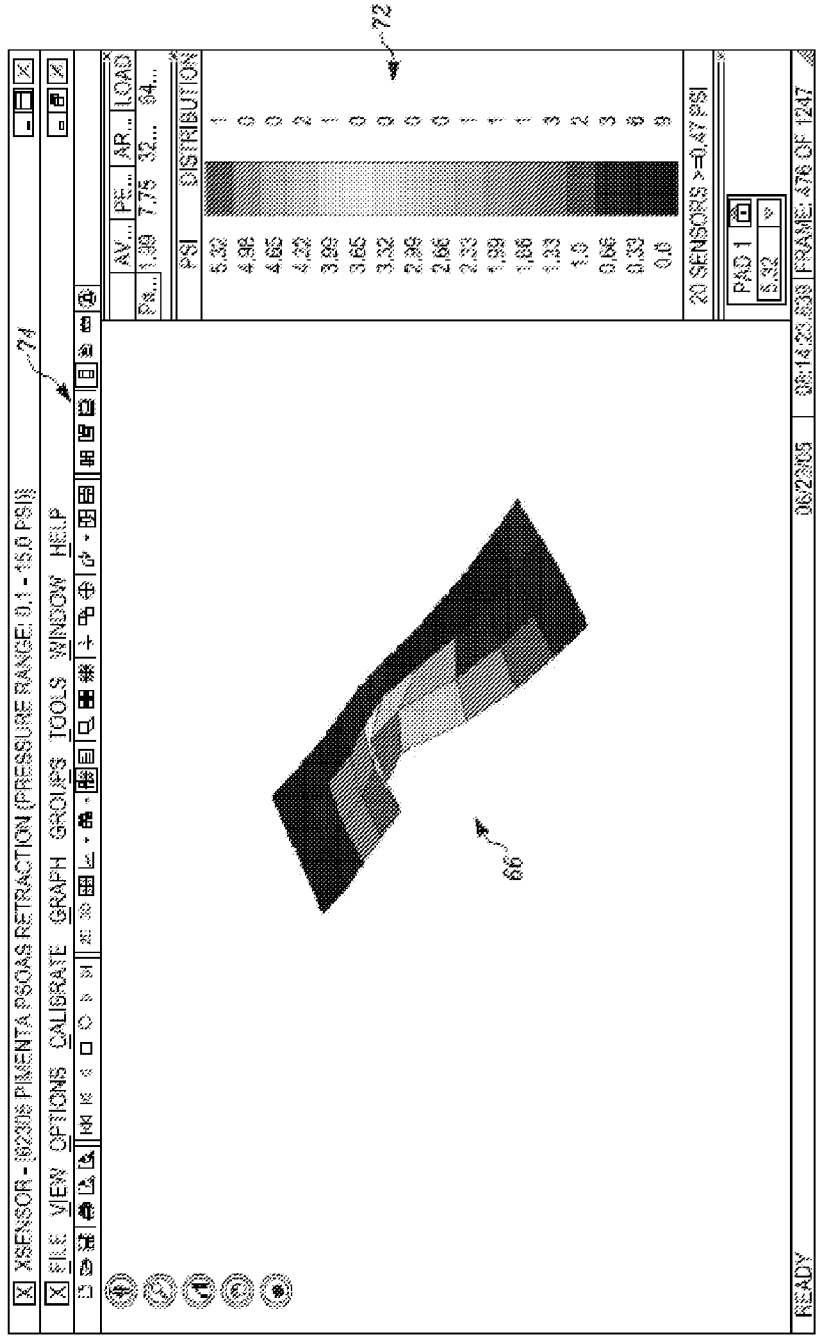
FIG. 16 is an exemplary full screen display of the 3-dimensional pressure mapping feature according to one embodiment of the present invention.
Figure 17:
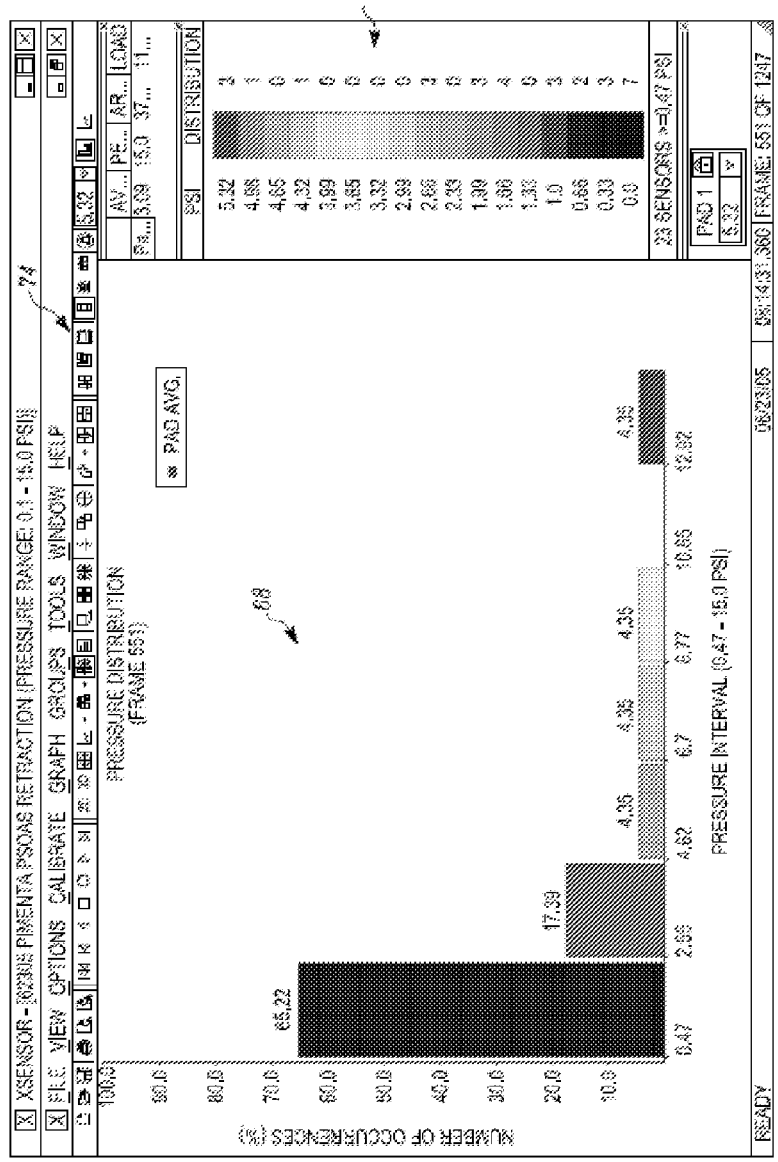
FIG. 17 is an exemplary full screen display of the pressure distribution chart feature according to one embodiment of the present invention.
Figure 18:
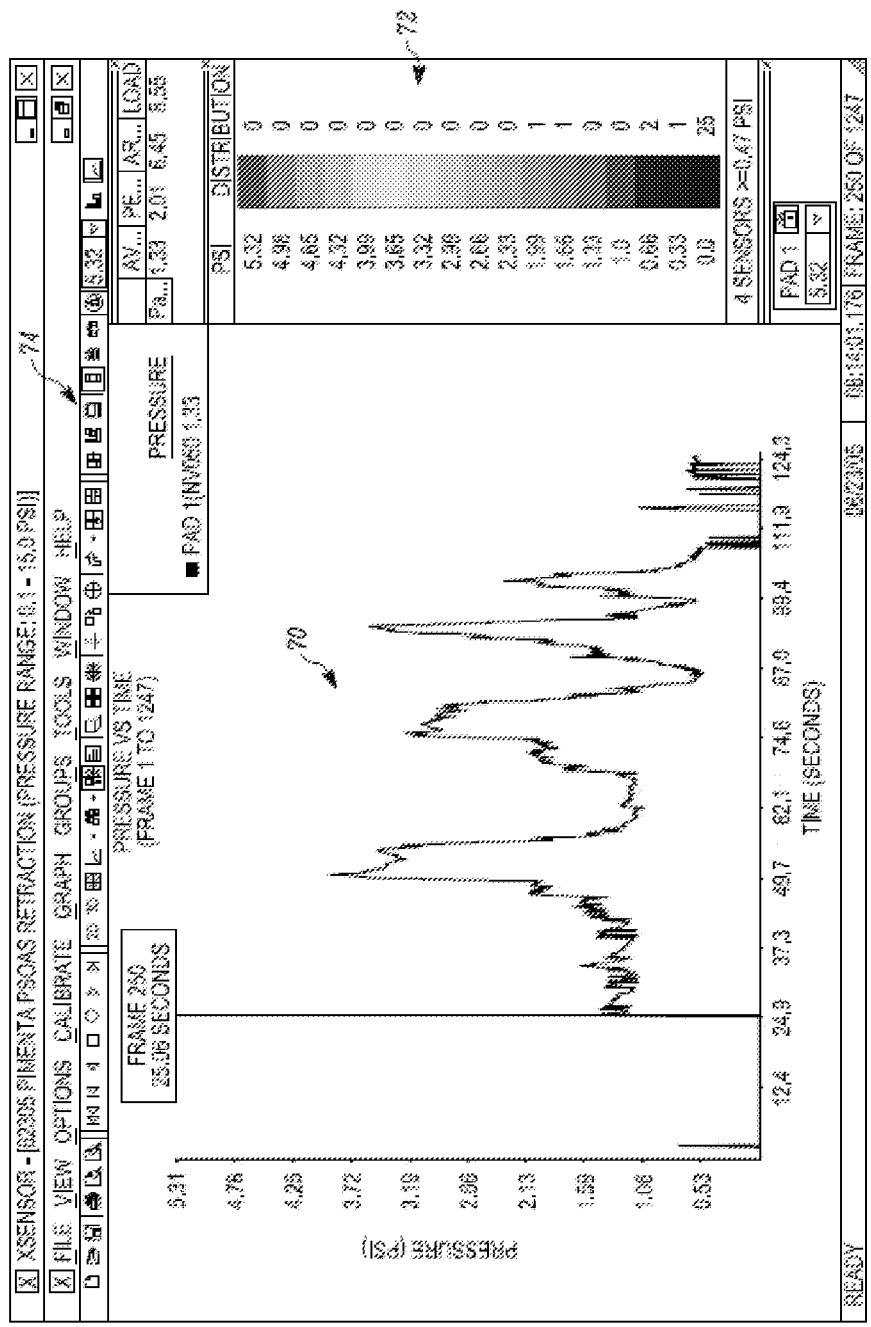
FIG. 18 is an exemplary full screen display of the pressure vs. time chart feature according to one embodiment of the present invention.

FIGS. 15-18 illustrate exemplary embodiments of the full screen displays. FIG. 15 is a full screen display of the 2-D grid map 64, wherein various colors are used (according to the legend 72) to indicate the amount of pressure measured for each grid unit on the sensor 56. A reference marker 76 is included which corresponds to a specific corner of the pressure sensor 56, to help orient the viewer. FIG. 16 illustrates the full screen display of the 3-D grid map, wherein various colors (according to the legend 72) are again used to indicate the amount of pressure measured on the grid units of sensor 56. FIG. 17 illustrates the full screen display of the pressure distribution graph 68, wherein the vertical axis indicates the percentage of grid units at the given moment which are under a measured pressure falling within the pressure intervals on the horizontal axis. FIG. 18 shows the full screen display of a PvT graph, wherein the maximum pressure measured on sensor 56 is charted against the retraction time.

Utilizing the various functions of the pressure mapping software, the surgeon may keep be kept aware to the extent which pressure is applied to a nerve throughout retraction, and also the length of time which a nerve is retracted. In addition, the 2-D and 3-D maps 64, 66 also allow the surgeon to quickly assess not only the extent and duration of the pressure, but also the position, orientation, and center mass of the nerve retractor 29 on the nerve. By way of example only, should either of the grid maps indicate that pressure is highest around one edge it may indicate that the nerve is not resting in the ideal position (e.g. centered and flat against the nerve engagement surface 46) and the surgeon may act to reposition the nerve relative to the nerve retractor. Pressure data collected by the processor 60 may preferably be viewed in real time, however, the processor 60 may also save the data for the entire procedure and the surgeon may go back and view any data from the same procedure at any time.

Figure 19:
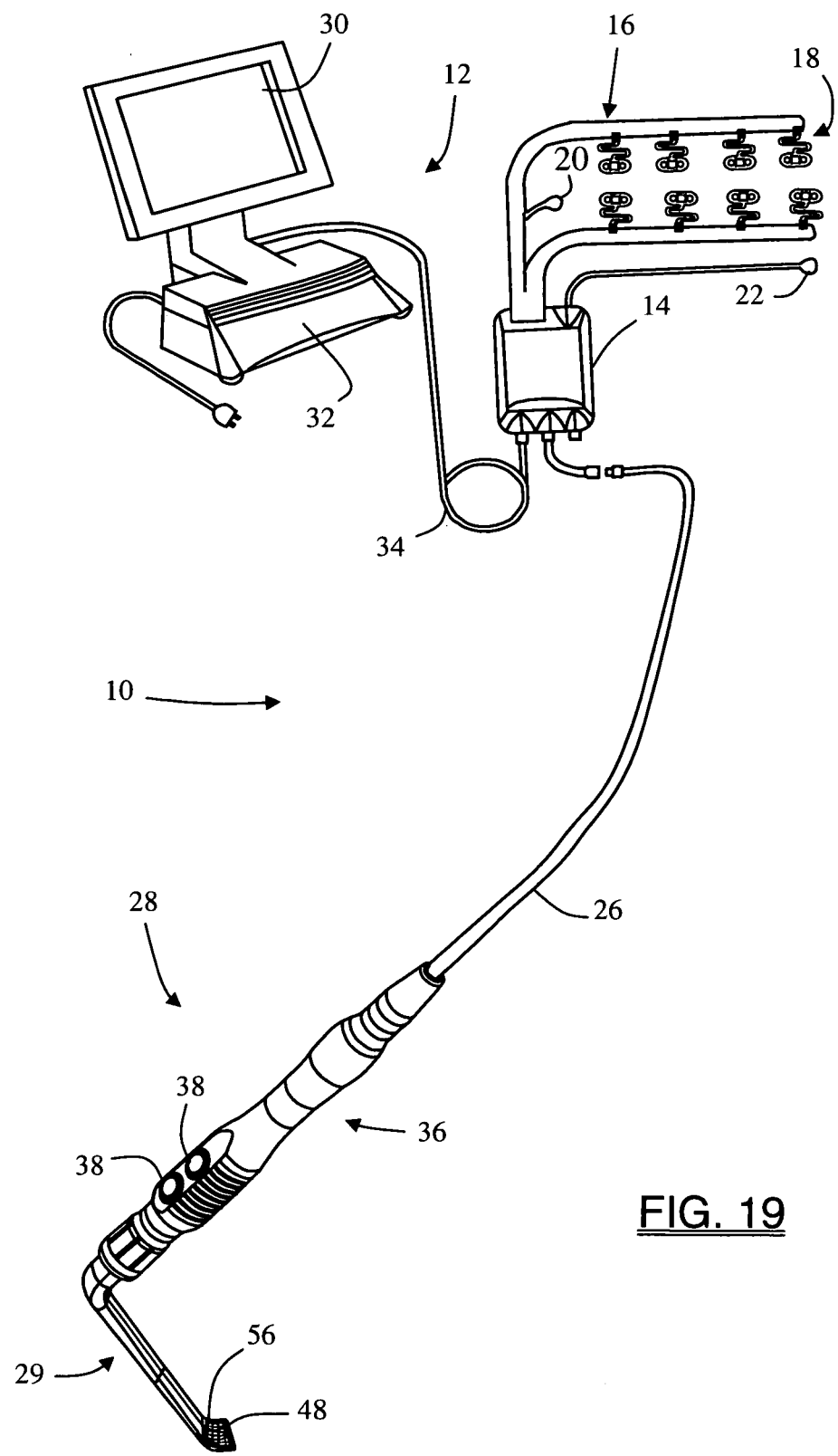
FIG. 19 is a perspective view of the system of FIG. 2 adapted to perform additional pressure sensing functions according to a different embodiment of the present invention.
Figure 20:
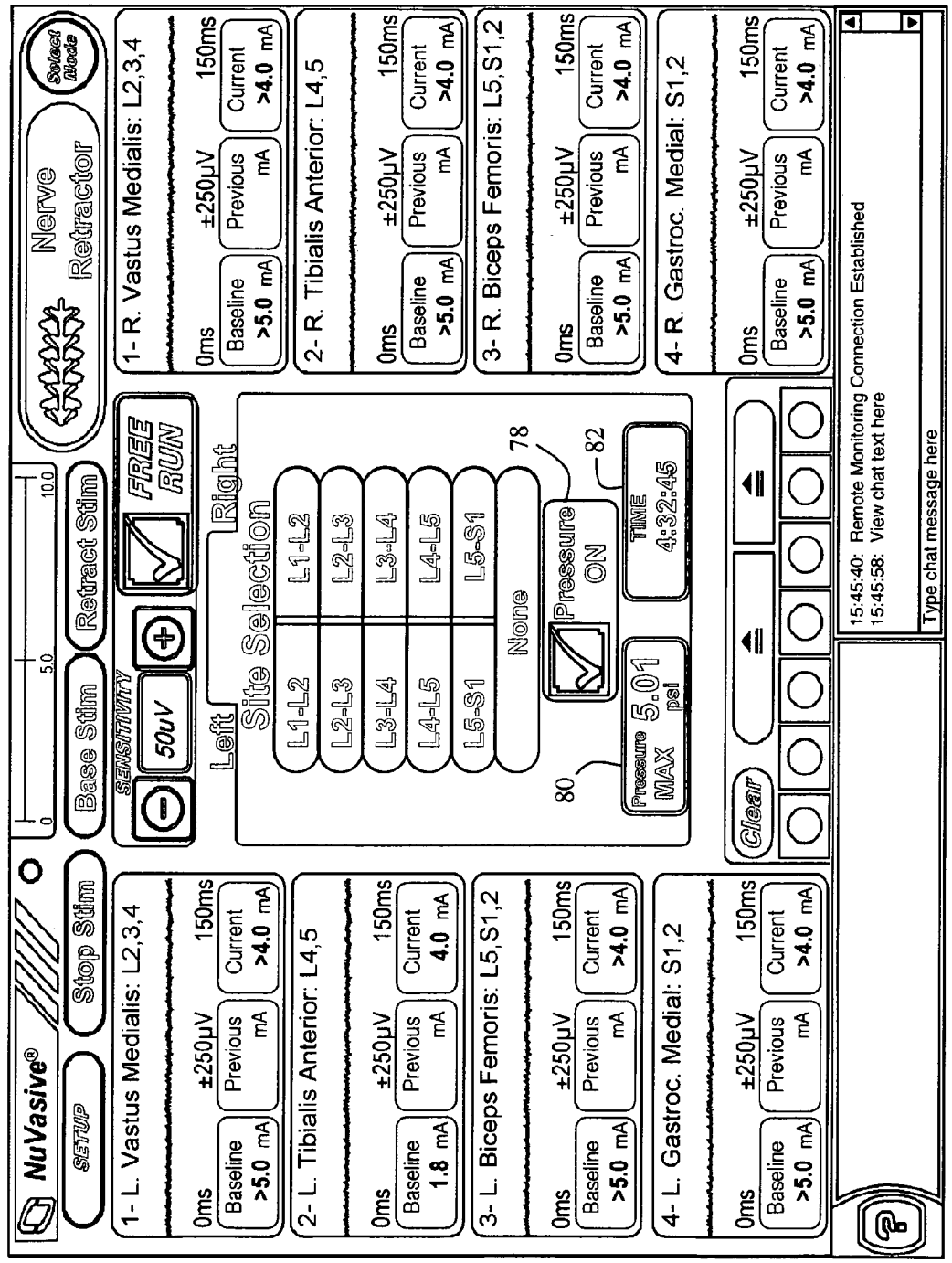
FIG. 20 is an exemplary screen display illustrating one embodiment of the Nerve Retractor mode for performing neural pathology monitoring augmented by pressure monitoring according to one embodiment of the present invention.

In another embodiment, set forth herein by way of example only and depicted in FIG. 19, the pressure sensing features of the system 10 are controlled via the control unit 12 and the pressure features may be fully integrated with the Nerve Retractor mode described above. In this embodiment, both the pressure sensor 56 and the stimulation electrode 48 are communicatively linked to the patient module 14 and pressure data is preferably viewed from within the Nerve Retractor screen display (discussed above with reference to FIG. 11). An embodiment of the Nerve Retractor screen display when system 10 is augmented with pressure sensing capabilities according to this embodiment is illustrated by way of example only in FIG. 20. In the example shown, the screen display includes, among its other features, a pressure selection tab 78 for initiating pressure monitoring (preferably at the same time nerve retraction) begins, a maximum pressure readout 80, and a timer readout 82. Selecting the pressure selection tab 78 using the GUI activates the pressure sensor 56 and starts the timer. The running time is displayed to the user in the timer readout 82. The maximum pressure measured on the sensor 56 is displayed with constant real time updating. Although not shown herein, it will be appreciated that any of a number of various features such as the 2-D and 3-D grid maps, pressure distribution, and pressure vs. time graph may also be generated and displayed in this embodiment. This may be accomplished, for example only, by providing one or more pop-up windows displaying the data and/or rearranging the screen view. Pressure data measured by the system 10 is recorded and saved such that it may be accessed again if necessary. Pressure data may also be included in procedure reports generated by the system 10 such that an accurate record is easily obtained.

While the pressure sensing features herein have been described above in terms of monitoring retraction pressure on nerves it will be understood that monitoring retraction pressure may be useful for any number of different body tissues which must be retracted out of the way during surgery. By way of example only, it may be extremely beneficial to monitor retraction pressure on the larynx and/or esophagus which must be retracted during anterior cervical procedure.

It may also be advantageous to communicate pressure related data captured by the system 10 to persons not present in the operating room. It is contemplated that the data may be transmitted (along with the nerve pathology and other neurophysiologic assessment data) to one or more remote locations and viewable by authorized persons. This may be accomplished by any number of data transmission methods. In one example, the data may be transmitted to a remote user via remote monitoring software such as that described in detail in the commonly owned and co-pending U.S. patent application Ser. No. 11/418,589, entitled "System and Methods for Performing and Monitoring Neurophysiologic Assessments," filed on May 5, 2006, the entire contents of which are incorporated by reference herein as if set forth in its entirety.

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the scope of the appended claims.

What is claimed is:

1. A system for assessing a pathology of a nerve, comprising:
    a nerve retractor having a nerve contacting portion with a plurality of pressure sensors and at least one stimulation electrode situated on said nerve contacting portion, said at least one stimulation electrode configured to deliver an electrical stimulation signal to a nerve within a patient;
    at least one sensor configured to detect neuromuscular responses evoked by said stimulation signal; and
    a processing unit communicatively linked to said pressure sensors and said at least one stimulation electrode and configured to calculate the pressure exerted by said nerve retractor on at least two locations along an outer surface of a nerve;
    said processing unit further including a display, wherein said display provides pressure mapping data in at least two dimensions based on said calculated pressure exerted on said at least two locations along said outer surface of said nerve.

2. The system of claim 1, wherein said display further provides at least one of additional alpha-numeric and graphic indicia relating to said calculated pressure.

3. The system of claim 2, wherein said additional alpha-numeric and graphic indicia includes at least one of maximum pressure value, time value, color, chart, and a graph.

4. The system of claim 1, wherein said stimulation electrode and said at least one sensor are communicatively linked to a control unit and said control unit is configured to determine a relationship between said stimulation signal and said neuromuscular response.

5. The system of claim 4, wherein said control unit includes a display and said display provides at least one of alpha-numeric and graphic indicia relating to said relationship.

6. The system of claim 4, wherein said relationship is a lowest stimulation current necessary to evoke a neuromuscular response.

7. The system of claim 6, wherein said control unit is further configured to perform a threshold hunting algorithm to identify the lowest stimulation current necessary to evoke said neuromuscular response.

8. The system of claim 7, wherein said stimulation electrode is positioned on said nerve retractor.

9. The system of claim 4, wherein said control unit and said processing unit are a single unit.

10. The system of claim 4, wherein said control unit and said processing unit are distinct units.

11. The system of claim 1, wherein said pressure mapping data is 3-dimensional pressure mapping data.

12. A system for retracting nerves during surgery, comprising:
    a nerve retractor having a distal portion including a nerve engagement surface, the nerve engagement surface having a plurality of pressure sensors situated thereon and a stimulation electrode;
    a processing unit linked to said pressure sensors and operable to determine an amount of pressure exerted on a nerve at at least two locations along said outer surface of said nerve when said nerve is engaged with said nerve engagement surface; said processing unit further including a display that provides pressure mapping data in at least two dimensions based on said calculated pressure exerted on said at least two locations along said outer surface of said nerve,
    said processing unit is further linked to said stimulation electrode and operable to a) direct a stimulation signal through said stimulation electrode and b) determine a relationship between said stimulation signal and a neuromuscular response elicited in response to said stimulation signal.

13. The system of claim 12, wherein said display further provides at least one of additional alpha-numeric and graphic indicia relating to said amount of pressure and at least one of alpha-numeric and graphic indicia relating to said relationship between said stimulation signal and said neuromuscular response.

14. The system of claim 13, wherein said relationship is a lowest stimulation current necessary to elicit said neuromuscular response.

15. The system of claim 12, wherein said nerve retractor further comprises a handle and said handle comprises a stimulation handpiece having at least one button operable to initiate said stimulation signal.

16. The system of claim 15, wherein said stimulation handpiece is removably attached to the distal portion.

17. The system of claim 16, wherein said stimulation handpiece threadably attaches to said distal portion.

18. The system of claim 13, wherein said at least one of additional alpha-numeric and graphic indicia relating to said determined pressure includes at least one of a maximum pressure value, time value, color, chart, and a graph.

19. The system of claim 12, wherein said control unit and said processing unit are distinct units.

20. The system of claim 12, wherein said pressure mapping data is 2-dimensional pressure mapping data.

* * * * *